US006759528B2

(12) United States Patent
Greenspan et al.

(10) Patent No.: US 6,759,528 B2
(45) Date of Patent: Jul. 6, 2004

(54) MAMMALIAN PRO-α3(V) COLLAGEN CHAIN GENES

(75) Inventors: Daniel S. Greenspan, Madison, WI (US); Yasutada Imamura, Yokohama (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 156 days.

(21) Appl. No.: 09/795,061

(22) Filed: Feb. 26, 2001

(65) Prior Publication Data

US 2003/0166842 A1 Sep. 4, 2003

Related U.S. Application Data

(60) Provisional application No. 60/186,510, filed on Mar. 2, 2000.

(51) Int. Cl.[7] .............................................. C07H 21/04

(52) U.S. Cl. ........................ 536/23.5; 536/23.1; 514/44

(58) Field of Search ............................... 536/23.1, 23.5; 514/44

(56) References Cited

PUBLICATIONS

Gupta, M. C. et al. (1997( Characterization of alpha1(IV) collagen mutations in Caenorhabditis elegans and the effects of alpha and alpha2(IV) mutations on type IV collagen distribution. J. Cell Biol. vol. 137, pp. 1185–1196.*

Ngo, J. T. et al. et al. (1994) "Computational complexity protein structure prediction, and the levinthal paradox" in "The protein folding problem and tertiary structure prediction". p. 491–495, Merz, Jr. K. et al. Eds. Birkhauser, Boston.*

Bouma, P. et al. (2001) COL5A1 exon 14 splice acceptor mutation causes a functional null allele, haploinsufficiency of alpha1(V) and abnormal heterotypic interstitial fibrils in Ehlers–Danlos syndrome II. J. Biol. Chem. vol. 273, pp. 13356–13364.*

Colman, P. M. (1994) Efects of amino acid sequence changes on antibody–antigent interaction. Res. Immunol. vol. 145, pp. 33–36.*

Schwarze, U. et al. (2001) Haploinsufficiency for one COL3A1 allele of type III procollagen results in a phenotype similar to the vascular form of Ehlers–Danlos syndrome, Ehlers–Danlos syndrome type IV. Am. J. Hum. Genet. vol. 69, pp. 989–1001.*

Imamura, Y., et al., "The Pro–α3(V) Collagen Chain," *The Journal of Biological Chemistry* 275:8749–8759 (2000).

Mann, K., "Isolation of the alpha–3–Chain of human type V collagen and characterization by partial sequencing, " *Hoppe–Seyler's* 373:69–75 (1992).

* cited by examiner

*Primary Examiner*—Christopher S. F. Low
*Assistant Examiner*—Samuel W. Liu

(57) ABSTRACT

Mammalian α3(V) pro-collagen and collagen polypeptides and variants thereof are encoded by exemplified polynucleotides. Investigative, diagnostic and therapeutic methods employ the polypeptides, polynucleotides and related materials, such as antibodies, sense- or antisense oligonucleotides and polynucleotides, and the like.

9 Claims, No Drawings

MAMMALIAN PRO-α3(V) COLLAGEN CHAIN GENES

CROSS-REFERENCE TO RELATED APPLICATIONS

This application claims the benefit of U.S. provisional application 60/186,510, filed on Mar. 2, 2000.

STATEMENT REGARDING FEDERALLY SPONSORED RESEARCH OR DEVELOPMENT

This work was supported by National Institutes of Health Grants GM46846 and AR43621. The US Government retains certain rights in the invention.

BACKGROUND OF THE INVENTION

Fibrils of the abundant collagen types I and II incorporate monomers of the low abundance fibrillar collagen types V and XI, respectively, which play a role in regulating type I collagen fibrillogenesis in vivo (1,2). Type V collagen helps regulate the size and shape of type I/V heterotypic fibrils (3–5). In some cases of classical Ehlers-Danlos Syndrome (EDS), a heritable connective tissue disorder, mutations in type V collagen genes (6–10) give rise to type I collagen fibrils of abnormal shape and diameter and cause connective tissue fragility, particularly in skin and joints. In chondrodysplasia, defects in a type XI collagen gene give rise to abnormal type II collagen fibrils (11).

Fibrillar collagens are synthesized as procollagen precursors with N- and C-propeptides that are proteolytically processed to yield mature monomers. Type V collagen is widely distributed in vertebrate tissues as an $\alpha1(V)_2\alpha2(V)$ heterotrimer (12,13) that helps regulate the diameters of fibrils of the abundant collagen type I. Previously, mutations in the human COL5A1 and COL5A2 genes, which encode the pro-α1(V) and pro-α2(V) chains, respectively, have been identified as the underlying defects in cases of the heritable connective tissue disorder classical EDS (Ehlers-Danlos Syndrome) (formerly EDS types I and II, see Reference (Ref.) 76). However, both COL5A1 and COL5A2 have been excluded in some cases of classical type I (EDS I), while a locus has yet to be identified for the hypermobility type of EDS (formerly EDS type III), a condition marked by gross joint laxity, recurrent joint dislocation, and chronic diffuse musculoskeletal pain not attributable to joint involvement.

Another type V collagen is an α1(V)α2(V)α3(V) heterotrimer, isolated primarily from placenta (17,18), but also reported in uterus, skin, and synovial membranes (12, 19–21). The α1(V)α2(V)α3(V) heterotrimer has remained poorly characterized but has a lower melting temperature than the $\alpha1(V)_2\alpha2(V)$ heterotrimer and may be incorporated into heterotypic fibrils. Type XI collagen, in the form of an α1(XI)α2(XI)α3(XI) heterotrimer (22), was first characterized as a minor collagen of cartilage. However, findings of type XI chains in noncartilaginous tissues (23), of type V chains in cartilage (24), and of cross-type heterotrimers composed of α2(V) and α1(XI) chains (25,26) now suggest that type V and type XI chains constitute a single collagen type in which different combinations of chains associate in a tissue-specific manner.

Complete primary structures of the type V/XI procollagen chains pro-α1(V), pro-α2(V), pro-α1(XI), and pro-α2(XI) are known (27–35). The pro-α3(XI) chain is thought to be an alternatively spliced product of the gene that encodes the pro-α1 chain of type II collagen (13, 24). Full-length cDNA sequences have provided not only the inferred primary structure of each chain, but have also provided probes that have allowed fine mapping of the expression domains of cognate mRNAs (27,36–41). Such studies are important, as the low levels of collagen type V/XI chains have limited biochemical and histochemical analyses of expression in developing and adult tissues. Nucleic acid probes have also enabled those studies which established the causal links between defects in type V/XI chains and genetic diseases (6–11).

Of the fibrillar procollagen chains, only the pro-α3(V) remains largely uncharacterized at the nucleotide and amino acid level. The α3(V) chain exhibits only limited distribution in mammals and is believed to be the least abundant fibrillar (type V/XI) collagen chain. The limited distribution may reflect a more specialized role than those of the other type V/XI chains. It is the only fibrillar (type V/XI) collagen or procollagen chain for which neither complete primary structure nor nucleic acid probes are available. About a third of the amino acid sequence of the major collagenous domain of the α3(V) chain was determined by N-terminal sequencing of proteolytic fragments (42). Nevertheless, a true understanding of the nature of mammalian type V/XI collagen and its roles in development, physiology, disease and treatment requires characterization the pro-α3(V) and α3(V) chains.

BRIEF SUMMARY OF THE INVENTION

The present invention is summarized in that mammalian α3(V) polypeptides and variants thereof are disclosed, as are recombinant materials, including genetic constructs, and methods for their production. The invention is further summarized in that polynucleotides that encode the polypeptides and the variants are also disclosed. The invention is still further summarized in that investigative, diagnostic and therapeutic compositions and methods employing the polypeptides, polynucleotides and related materials, such as antibodies, sense- or antisense oligonucleotides and polynucleotides, and the like, are also disclosed. The chromosomal map positions in humans and mice of the polynucleotides that encode the mammalian α3(V) polypeptides are also disclosed.

It is an object of the present invention to enable production of large quantities of mammalian α3(V) polypeptide chains for research, diagnostic and therapeutic use.

It is an advantage of the present invention that collagen comprising mammalian pro-α3(V) or α3(V) chains can be synthesized for any such use.

Other objects, features and advantages of the present invention will become apparent upon consideration of the following detailed description taken in conjunction with the accompanying drawings.

BRIEF DESCRIPTION OF THE SEVERAL VIEWS OF THE DRAWINGS

Not applicable.

DETAILED DESCRIPTION OF THE INVENTION

As used herein, a "mammalian α3(V) polypeptide" refers to a modified or unmodified polypeptide having an amino acid sequence characteristic of those shown in SEQ ID NO:2 and SEQ ID NO:4, or a novel fragment thereof, especially a fragment that is antigenic or has a biological activity. Preferably, a mammalian α3(V) polypeptide exhibits at least one biological activity of mammalian α3(V) procollagen or collagen. A mammalian α3(V) polypeptide can be a mature protein or a larger protein that can include native or non-native amino acid sequences at the N- or C-terminus or both, a propeptide sequence, or other sequence attached to the mature polypeptide sequence. These sequences can include amino acid sequences that assist in purification, detection, or stabilization of the mammalian α3(V) polypeptide.

Within the scope of the invention are polypeptides that have at least 80% amino acid identity to that of either SEQ ID NO:2 or SEQ ID NO:4 over its entire length, and more particularly polypeptides having at least 90% identity, or more preferably at least 95% identity, to that of SEQ ID NO:2 or SEQ ID NO:4, when the sequences are aligned to obtain the highest order match using published techniques. Most preferred are polypeptides having between 97 and 99% amino acid identity to that of SEQ ID NO:2 or SEQ ID NO:4. The term "identity" is given its art recognized meaning. Sequence identity can be determined, for example, using the methods disclosed by Devereux et al. (83), incorporated herein by reference in its entirety.

An polypeptide is, e.g., 80% "identical" if it contains up to 20 amino acid sequence differences, changes or alterations (including substitutions, deletions, or insertions) per each 100 amino acids in reference sequences SEQ ID NO:2 or SEQ ID NO:4. The differences, changes or alterations can be at any position in the amino acid sequence of either polypeptide and can be interspersed as individual changes or contiguous differences.

A "mammalian α3(V) polynucleotide" refers to a polynucleotide that encodes any mammalian α3(V) polypeptide, or a polynucleotide fragment thereof, or a complement of any of the foregoing. A polynucleotide can be modified or unmodified DNA or RNA, whether fully or partially single-stranded or double-stranded or even triple-stranded. A modified polynucleotide can be chemically or enzymatically induced and can include so-called non-standard bases such as inosine. A preferred polynucleotide comprises any sequence that can encode a polypeptide of SEQ ID NO:2 or SEQ ID NO:4, where the number of such polynucleotides is substantial, in view of the well-known degeneracy in the genetic code. In a most preferred embodiment, the polynucleotide comprises a sequence of polypeptide-encoding nucleotides shown in SEQ ID NO:1 (bases 82 to 5298) or SEQ ID NO:3 (bases 87 to 5321), or is a polynucleotide fragment or complement of any of the foregoing.

Within the scope of the invention are polynucleotides that comprise nucleotide sequences having at least 80% identity to that of any of the foregoing over its entire length, and more preferably polynucleotides comprising sequences having at least 90% identity, or more preferably at least 95% identity, to that of SEQ ID NO:1 or SEQ ID NO:3, when the sequences are aligned to obtain the highest order match using published techniques. A polynucleotide sequence is, e.g., 80% identical if it contains up to 20 nucleotide differences, changes or alterations (including substitutions, deletions, or insertions) per each 100 nucleotides in reference sequences SEQ ID NO:1 or SEQ ID NO:3. The differences, changes or alterations can be at any position in the nucleotide sequence of either polynucleotide and can be interspersed as individual changes or contiguous differences.

Identified herein are certain fragments of the mouse and human polypeptides that were not previously known. These include SEQ ID NO:2 between amino acids 1 and 477, SEQ ID NO:2 between amino acids 564 and 663, SEQ ID NO:2 between amino acids 709 and 721, SEQ ID NO:2 between amino acids 758 and 785, SEQ ID NO:2 between amino acids 819 and 923, SEQ ID NO:2 between amino acids 1008 and 1052, SEQ ID NO:2 between amino acids 1086 and 1245, SEQ ID NO:2 between amino acids 1287 and 1310, SEQ ID NO:2 between amino acids 1334 and 1739, SEQ ID NO:4 between amino acids 1 and 478, SEQ ID NO:4 between amino acids 565 and 664, SEQ ID NO:4 between amino acids 710 and 722, SEQ ID NO:4 between amino acids 759 and 786 , SEQ ID NO:4 between amino acids 820 and 924, SEQ ID NO:4 between amino acids 1009 and 1053, SEQ ID NO:4 between amino acids 1087 and 1246, SEQ ID NO:4 between amino acids 1288 and 1311, and SEQ ID NO:4 between amino acids 1335 and 1745. Polypeptides having at least 80% identity to those polypeptide fragments, and preferably having at least 90%, 95%, 97% and 99% identity, are also within the scope of the invention, as are polynucleotides that encode any such polypeptide fragment.

The invention also includes polynucleotides that hybridize to any of the aforementioned polynucleotides under stringent conditions, such as overnight incubation at 42° C. in a solution comprising 50% formamide, 5×SSC (150 mM NaCl, 15 mM sodium citrate), 50 mM sodium phosphate (pH 7.6), 5× Denhardt's solution, 10% Dextran Sulfate, and 20 micrograms/ml denatured, sheared salmon sperm DNA, followed by washing the filters in 0.1×SSC at about 65° C. Polypeptides encoded by any of the foregoing polynucleotides are also within the scope of the invention.

The polynucleotide can also be a variant of any of the foregoing. A "variant" as the term is used herein, is a polynucleotide that differs from a reference polynucleotide but retains essential properties. Generally, differences are limited so that the sequences of the reference polypeptide or polynucleotide and the variant are closely similar overall and may be identical in part. A variant and reference polypeptide may differ in amino acid sequence by one or more substitutions, additions, deletions in any combination. A substituted or inserted amino acid residue may or may not be one encoded by the genetic code. A variant of a polynucleotide differs in nucleotide sequence from a reference polynucleotide. A variant polynucleotide may or may not encode an amino acid sequence that differs from the amino acid sequence encoded by the reference polynucleotide. Nucleotide changes can, but need not, result in amino acid substitutions, additions, deletions, fusions and truncations in the polypeptide encoded by the reference sequence. A variant of a polynucleotide or polypeptide can be a naturally occurring allelic variant, or can be a variant that is not known to occur naturally. Non-naturally occurring variants of polynucleotides may be made by mutagenesis techniques or by direct synthesis or other method.

In keeping with the present invention, exemplary amino acid sequences of mammalian pro-α3(V) proteins, precursors of mammalian α3(V) proteins, are disclosed, as are cDNA sequences that encode the exemplified human and murine amino acid sequences. Patterns of expression in developing and adult tissues are examined, and the chromosomal locations of the cognate mouse Col5a3 and human COL5A3 genes are mapped. Full length mammalian pro-α3(V) cDNA sequences from mice and humans are disclosed in SEQ ID NO:1 and SEQ ID NO:3, respectively. Pro-α3(V) chain encoded by the exemplified murine and human nucleic acid sequences are disclosed in SEQ ID NO:2 and SEQ ID NO:4, respectively. The full-length mouse pro-α3(V) cDNA and amino acid sequences will be available at GenBank Accession No. AF176645. The full-length human pro-α3(V) cDNA and amino acid sequences will be available at GenBank Accession No. AF177941.

The disclosed amino acid sequences have all of the indicia of procollagen chains. Signal peptide cleavage sites, predicted by the method of Nielsen et al. (82), are after amino acid residue 30 (Ala) in the mouse protein and after amino acid residue 29 (Ala) in the human protein. Pro-α3(V) is closely related to the α1(V) precursor, pro-α1(V), but with marked differences in N-propeptide sequences, and collagenous domain features that provide insights into the low melting temperature of α1(V)α2(V)α3(V) heterotrimers, lack of heparin binding by α3(V) chains and the possibility that α1(V)α2(V)α3(V) heterotrimers are incorporated into heterotypic fibrils.

In a related aspect, any polynucleotide sequence of the present invention, or an antisense version thereof, can be provided in a vector or genetic construct in a manner known to those skilled in the art. A polypeptide-encoding polynucleotide so provided in a vector can, but need not, be under the transcriptional control of one or more regulatory elements which can include a promoter not natively found adjacent to the polynucleotide such that the encoded polypeptide can be produced when the vector is provided in a compatible host cell or in a cell-free transcription and translation system. Such cell-based and cell-free systems are well known to the skilled artisan. Cells comprising a vector containing a polynucleotide of the invention are themselves within the scope of the invention.

Collagen and derivatives of collagen (gelatin) have been used in medical, pharmaceutical and consumer products for about 40 years. Examples of approved use of collagen include hemostats, vascular sealants, tissue sealants, implant coatings, injectable for plastic surgery, food additives, dental implants, artificial dura, wound dressings, antiadhesion barriers, antibiotic wound dressing, and platelet analyzer reagents. Human and animal collagen can be recombinantly reproduced. The disclosure of the full-length mouse pro-α3(V) cDNA and the full-length human pro-α3(V) cDNA in the present invention makes it possible to recombinantly reproduce human and animal collagen α3(V), which can be used in the applications described above. In addition, human pro-α3(V) has been found to express in many tissues including mammary gland, placenta, uterus, brain, fetal lung, and fetal and adult heart. The present invention allows the reproduction of collagen α3(V) for the purpose of matching its natural role in the body. Thus, if any of the above tissue is damaged, collagen α3(V) can be produced and used in the tissue repairing process.

The polynucleotides of the invention can also be employed as diagnostic reagents in assays for diagnosing a disease or susceptibility to a disease associated with α3(V) chains in human or non-human animals. Assays for detecting mutations in protein-encoding sequences are well known to the skilled artisan and can include assaying for changes in primary structure of a fragment by nucleotide sequence analysis, by digesting mismatched hybrids with RNase or by measuring changes in hybrid melting temperatures. Changes in sequence length resulting from insertion or deletion can be observed as a change in electrophoretic mobility of amplified fragments. The present invention also enables other methods for diagnosing changes in an α3(V)-encoding polynucleotide, such as nuclease protection assays, for one of ordinary skill in the art. A skilled artisan understands that such assays for diagnosing genetic changes at a fine scale in polynucleotides that encode α3(V) chains can be facilitated by providing an array of fragments of the polynucleotides of the invention for systematic screening in parallel for changes at any of a plurality of positions. This methodology enables an association between one or more mutations and a susceptibility to a disease such as classical or hypermobility type of EDS or diseases of other tissues in which α3(V) expression is noted such as diseases of female reproductive tissues or the heart as well as various other genetic diseases of the musculoskeletal system, connective tissue or skin.

The present invention also enables one to diagnostically determine whether a human or non-human animal exhibits an altered (e.g., increased or decreased) amount of an α3(V) chain or an mRNA that encodes α3(V) in one or more tissues of interest. Methods for measuring polynucleotide levels are well known in the art and include quantitative PCR, Northern blotting, dot blotting and others. Methods for measuring protein levels are also known and include ELISA, radioimmunoassay, competitive-binding assays and Western blotting.

Thus, the invention is also embodied in a diagnostic kit comprising one or more of any polynucleotide of the invention, a complementary sequence (antisense) to any polynucleotide of the invention, a polypeptide of the invention, or an antibody or single chain antibody against a polypeptide of the invention or against an immunogenic fragment thereof. An antibody can be obtained in any of several well-known methods such as hybridoma or trioma techniques and can also have utility in purifying α3(V) polypeptides or in treating diseases associated with the presence of α3(V).

An immunological response effective to protect a human or non-human mammal against undesired activities of wild type or mutant α3(V) polypeptides can also be raised in vivo by administering to the mammal an immunogenic polypeptide (either directly or by administering to the mammal a genetic vector comprising sequences that direct expression of the polypeptide under the control of a transcriptional promoter). A vaccine of this type can also include a suitable carrier or adjuvant and can be administered at standard dosages according to standard protocols. The vaccine is preferably administered parenterally by injection, but can also be administered by any route known to be effective for inducing an immune response.

The polypeptides of the invention also enable a skilled artisan to screen for agonists and antagonists of the polypeptides that can be selected using standard screening protocols that include the steps of expressing the polypeptide in or on suitable host cells, exposing the cells to various test compounds, and observing whether any test compound binds to the polypeptide or stimulates or inhibits any biological activity of the polypeptide relative to the binding or activity of the polypeptide in or on untreated control cells. The host cells can be any cells capable of expressing the polypeptide and can include mammalian cells, insect cells, yeast cells, or bacterial cells. Envisioned agonists and antagonists can include, but are not limited to, fragments of the full-length pro-α3(V) or α3(V) polypeptides that compete biologically with the full-length polypeptides as well as ligands, enzymes, receptors and the like that block active sites on the polypeptides and prevent their interaction with other molecules.

In another aspect, then, the invention extends to a screening kit for identifying agonists or antagonists of the polypeptides of the invention, where the kit contains at least one polypeptide of the invention, an isolated cell or portion of a cell (such as a cell membrane) that contains a polypeptide of the invention, or an antibody to a polypeptide of the invention. In yet another aspect, agonists and antagonists so obtained are within the scope of the invention.

In a therapeutic method, an agonist or antagonist can also be administered along with a pharmaceutically acceptable carrier to enhance or inhibit, respectively, a biological activity of the pro-α3(V) or α3(V) polypeptides. If the agonist or antagonist is itself a polypeptide or oligopeptide, it can be administered directly (with or without a suitable pharmaceutical carrier) or can be produced in vivo after administration of an expressible genetic vector that encodes the agonist or antagonist or a cell that contains the expressible genetic vector. Alternatively, expression of the pro-α3 (V) or α3(V) polypeptides can be inhibited by administering an antisense sequence of the present invention to interfere with normal polypeptide expression. The antisense sequence can be administered directly (with or without a carrier) or can be produced in vivo after administration of a genetic vector capable of transcribing antisense genetic sequences. Appropriate dosages of an agonist or antagonist will vary depending upon the route of administration and the activity of the administered compound, but can readily be determined and optimized by a skilled artisan. Dosages in the range of between about 0.1 and 100 μg/kg are generally appropriate.

EXAMPLE 1

Murine pro-α3(V) cDNA sequence

The following steps were performed to obtain a full-length cDNA sequence of murine pro-α3(V). A BLAST search of the dbEST database of expressed sequences tags, using query sequence LGPPGEDGAXGSVGPT-GLPGDLGPPGDPGVSGIDG (SEQ ID NO:4; amino acids 1246–1280) from a human α3(V) peptide TSK5/K1 (42), located 459-bp of α3(V) triple helix-encoding sequences from a mouse mammary gland EST (IMAGE clone 1366609; GenBank Accession No. AI021711). The EST clone was obtained from the IMAGE Consortium, sequenced in its entirety, and found to contain an insert of 2259-bp corresponding to roughly the 3'-most third of the final full-length mouse pro-α3(V) cDNA sequence (SEQ ID NO:1; nt 3850–6108).

Primer 5'-GGTCCCACAGGACTCCCTGGAGATCT-3' (forward, SEQ ID NO:1, nt 3853–3878) and primer 5'-TAGCCCAGGAGGTCCCAGGAGACCTG-3' (reverse, reverse complement of SEQ ID NO:1, nt 4209–4184), corresponding to EST sequences, amplified a 357 bp PCR product, using a mouse 17 days postcoitus (dpc) embryo cDNA 5' stretch λgt10 library (Clontech) as template. This product was used to screen the same λgt10 library, yielding one positive clone (ME7) with a 1742-bp insert.
Sequences of clone ME7 overlapped those of the EST clone and contained an additional 422-bp at the 5'-end.

A 304-bp EcoRI fragment from the 5'-portion of the clone ME7 insert was used as a probe for further screening of the 17 dpc embryo library, yielding two additional clones, ME8-11 (1059-bp insert) and ME3-5 (876-bp insert), with 606-bp and 423-bp of additional 5' sequences, respectively.

Next, 5' rapid amplification of cDNA ends (RACE) was performed with two nested pro-α3(V)-specific reverse primers, 5'-CCTTCAAACCAATGGGTCCTGGGTCT-3' (reverse complement of SEQ ID NO:1; nt 3061–3036) and 5'-CAATGCCACCAGAGGGGCCTACAGGA-3' (reverse complement of SEQ ID NO:1; nt 3142–3117), corresponding to sequences near the 5'-end of clone ME8-11, using the Marathon cDNA Amplification Kit and mouse brain Marathon-Ready cDNA template, according to the manufacturer's protocol (Clontech). This nested 5' RACE produced a 613 bp product.

To obtain further mouse sequences, two pro-α3(V)-specific reverse primers corresponding to sequences near the 5'-end of the 613 bp 5' RACE product, 5'-CTTTCT CCCCCAGTGGTCCCAAGGGT-3' (primer MSP3, reverse complement of SEQ ID NO:1; nt 2530–2505) and 5'-CCGGTGTGCCGCGTTCTCCTTCCTCT-3' (primer MSP4, reverse complement of SEQ ID NO:1; nt 2584–2559), were used both for a further nested 5' RACE, performed as above, but in addition using Advantage-GC cDNA Polymerase Mix (Clontech); and for nested PCR using 17 dpc embryo λgt10 library cDNA as template and a λgt10 vector-specific primer, 5'-TCCCCACCTTTTGAG CAAGTTCAGCCT-3' (SEQ ID NO:5).

Nested PCR with the λgt10 primer and library yielded a product with 898 bp of pro-α3(V) sequences. The 5'-RACE products were subcloned into the pGEM-T vector (Promega). A forward PCR primer, 5'-GTGACAGGGAGTGATGGCGCACCA-3' (SEQ ID NO:1; nt 1930–1953), corresponding to sequences within the 898 bp PCR product, and reverse primer MSP3 (see above) were used as a primer set for PCR screening of the 5'-RACE product-pGEM-T clones. One clone, which contained a 2530 bp PCR insert, was found to contain the remainder of mouse pro-α3(V) coding sequences plus 81-bp of the 5'-untranslated region (UTR).

EXAMPLE 2

Human pro-α3(V) cDNA sequence

To obtain human pro-α3(V) sequences, a human placenta cDNA λgt11 library (Clontech) was screened with a 562-bp EcoRI cleavage fragment of the mouse IMAGE clone, roughly corresponding to the complete pro-α3(V) C-propeptide coding sequences. One positive clone (HP3-2) had a 3382-bp insert that corresponded to the 3'-half of human pro-α3(V) coding sequences plus 820-bp of 3'-UTR. A BLAST search of the dbEST database, using mouse pro-α3(V) C-propeptide sequences as the query sequence, located human retina EST pro-α3(V) sequences (EST19755, clone HARAL32, GenBank Accession No. AA317772, ATCC Item No. 118234). The EST clone was obtained from the American Type Culture Collection, sequenced in its entirety, and found to have an insert of 1316-bp that overlapped the 3'-end of clone HP3-2 and included an additional 34-bp of 3'-UTR extending to a poly(A) tail.

Pro-α3(V)-specific reverse primers 5'-TCACCT AGAGGTCCCACTTCTCCTGTCT-3' (reverse complement of SEQ ID NO:3; nt 2884–2857) and 5'-AGTTCTCCTCTCTGTCCAGGGTGCCCT-3' (reverse complement of SEQ ID NO:3; nt 2797–2771), corresponding to sequences near the 5'-end of λgt11 clone HP3-2, were used for nested 5' RACE with Marathon-ready human fetal brain cDNA as template, resulting in a product containing 366-bp of pro-α3(V) sequences. A subsequent nested PCR with pro-α3(V)-specific reverse primers 5'-GCTGCCCTGTCTTTCCCGACTTCCCT-3' (reverse complement of SEQ ID NO:3; nt 2562–2537) and 5'-ACCGGGAAATCCAATAGATCCCTTAGGT-3' (reverse complement of SEQ ID NO:3; nt 2513–2486), corresponding to sequences near the 5'-end of the 366 bp RACE product, and using a λgt10 vector-specific primer 5'-AGATTGGGGGTAAATAACAGAGGTGGCT-3' (SEQ ID NO:6) and λgt10 human Fetal Heart cDNA library template, produced a product containing 774-bp of pro-α3 (V) sequences.

Next, nested 5' RACE with pro-α3(V)-specific reverse primers 5'-ACCCTTCTCCCCAGGAGTGCCAATGAGT-3' (reverse complement of SEQ ID NO:3; nt 2081–2054) and 5'-ACCCATGGTTTCCCTGCTGTCCCGGA-3'0 (reverse complement of SEQ ID NO:3; nt 2028–2003), corresponding to sequences near the 5'-end of the 774-bp product, and using Marathon-Ready human heart cDNA template, yielded a 1532-bp product. This was followed by another nested 5' RACE with pro-α3(V)-specific reverse primers 5'-TCACAAGCCTGGAAGGCGGCCTGAGGA-3' (reverse complement of SEQ ID NO:3; nt 739–713) and 5'-GGGTCCCCAGCACAGTGAGTCCAGCTA-3' (reverse complement of SEQ ID NO:3; nt 654–628), and using Marathon-Ready human heart cDNA template, which yielded a 551-bp product.

A final nested 5' RACE with pro-α3(V)-specific reverse primers 5'-AGTTCTCAGGAAAGTGGCCTTCTGGAA-3' (reverse complement of SEQ ID NO:3; nt 354–328) and 5'-GCACACCCAGGGCCTTCAGGACATCCA-3' (reverse complement of SEQ ID NO:3; nt 207–181), corresponding to sequences near the 5'-end of the 551-bp product, and using Marathon-Ready human placenta cDNA template and Advantage-GC cDNA Polymerase Mix (Clontech), produced a 207-bp product that contained remaining pro-α3(V) coding sequences plus 86-bp of 5'-UTR.

First rounds of nested RACE PCRs were performed in 50 μl reactions with 20 pmol of each primer, 5 μl of Marathon cDNA, and 1 μl of Advantage cDNA Polymerase Mix (Clontech) at 95° C./3 min followed by 40 cycles of 95° C./20 sec, 68° C./30 sec, 72° C./2–4 min and final extension at 72° C./7 min. When Advantage-GC cDNA Polymerase Mix was used, GC-Melt was added to a final concentration of 1 M per reaction. First rounds of nested PCRs using λgt10 primers were performed the same way as first round RACE PCRs, except that the annealing temperature was 70° C., and template was 5 ul of a λgt10 library that had been diluted 12-fold with water and heat-denatured by boiling for 10 min. The second nested rounds of RACE PCRs and second nested rounds of PCRs using λgt10 primers, were performed the same way as first rounds, except that 25, rather than 40, cycles were used and template was 5 ul of first round PCR products diluted 50-fold with water.

The full-length mouse and human prepro-α3(V) collagen chain sequences, inferred from cDNA clones and PCR products described in Experimental Procedures, are presented in SEQ ID NO:1 and SEQ ID NO:3, respectively. The human and mouse prepro-α3(V) chains comprise 1745 and 1739 amino acid residues, respectively. In each case, the mature form of the protein extends from amino acid 30 to the terminal residue 1745 or 1739, respectively.

These sequences show pro-α3(V) to be related to the pro-α1(V), pro-α1(XI), and pro-α2(XI) chains, with sequence similarities and differences that provide insights into the nature and biology of the pro-α3(V) chain. As an example, a conserved Lys at position 84 of the COL1 domain suggests that α1(V)α2(V)α3(V) heterotrimers may be incorporated into heterotypic fibers, while differences in N-propeptide/telopeptide sequences suggest that such heterotypic fibrils would have different surface charge properties than heterotypic fibrils which incorporate $\alpha1(V)_2\alpha2(V)$ heterotrimers, likely to influence fibril shape/diameters and interactions with other macromolecules.

An unexpected finding was the expression of pro-α3(V) RNA primarily in the connective tissue sheaths (epimysia) of forming muscles and in the rudiments of ligamentous attachments adjacent to forming bones and within nascent joints during development. This observation coupled with the fact that pro-α3(V) chains combine with pro-α1(V) and pro-α2(V) chains to form heterotrimers, suggests COL5A3 as a possible candidate locus for at least some cases of classical EDS in which COL5A1 and COL5A2 have been excluded, and for at least some cases of the hypermobility type of EDS. Expression of pro-α3(V) in epimycium also raises the possibility that defects in COL5A3 and Col5a3 might result in some muscle myopathies, as has recently been shown to be the case with the genes for type VI collagen (81).

The pro-α3(V) chains presented in SEQ ID NO:2 and SEQ ID NO:4 are most similar to, but are distinct from, the pro-α1(V), pro-α1(XI) and pro-α2(XI) fibrillar procollagen chains. The human and mouse prepro-α3(V) chains comprise 1745 and 1739 amino acid residues, respectively. Each includes a 1011 amino acid major collagenous domain (COL1), which is shorter than the COL1 domains of the other vertebrate fibrillar collagen chains. In COL1, for example, the pro-α3(V) COL1 domain is most similar to that of pro-α1(V)(76% similarity, 71% identity), but only slightly less similar to that of pro-α1(XI)(74% similarity, 70% identity) and only somewhat less similar to that of pro-α2(XI)(72% similarity, 67% identity) when comparison was via the Genetics Computer Group GAP program (83). The shorter COL1 domain, coupled with its smaller number of amino acid residues than are found in the pro-α1(V) and pro-α2(V) COL1 (215 PRO codons versus 249 and 223 PRO codons, respectively), helps explain the lower melting temperature of pepsinized α1(V)α2(V)α3(V) heterotrimers compared to that of pepsinized $\alpha1(V)_2\alpha2(V)$ heterotrimers (18,67).

The 412 amino acid residue region between the signal peptide and COL1 domain can be divided into four subdomains. Immediately upstream of the COL1 domain is a short non-collagenous linker region, and immediately N-terminal of this is a short collagenous domain which corresponds to the NC2 (noncollagenous 2) and COL2 domains, respectively. The pro-α3(V) COL2 domain is likely to form a shorter triple helix than those formed by the COL2 domains of the other procollagen chains of this subfamily.

A large globular region between the pro-α3(V) signal peptide and the COL2 domain corresponds to an NC3 domain found in other members of this subfamily. NC3 can be roughly divided into two subdomains, namely (1) an amino terminal PARP (proline/arginine-rich protein) between the signal peptide and two clustered cysteines and (2) a variable region between PARP and COL2.

The pro-α3(V) PARP domain retains four cysteines conserved among all members of the subfamily, but has a markedly acidic pI of 4.4, unlike the highly basic pI predicted from the sequence of the PARP domain of pro-α2 (XI). This suggests a somewhat different function for pro-α3(V) and α3(V) chains than for the other family members.

Little or no homology exists between the related proteins in the variable region and may reflect differences in biological activities. The residues of the α3(V) variable region appear to protrude beyond the surface of heterotypic fibrils and may directly control fibrillogenesis by sterically hindering the further addition of collagen monomers to the fibril surface. These protruding sequences may also help modulate interactions between heterotypic collagen fibrils and other components of the extracellular matrix. The pro-α3(V) variable domain has a highly basic predicted pI (e.g. 10.3 for the human sequence) and a total absence of tyrosines. This is predicted to affect the charge properties of the α3(V) chains which may in turn alter the charge properties and surface characteristics of α1(V)α2(V)α3(V) heterotrimers from those of $\alpha1(V)_2\alpha2(V)$ heterotrimers.

Canonical RX(K/R)R furin cleavage sites (56,57) just C-terminal of the COL1 in the human and mouse pro-α3(V) chains align with that of the pro-α1(V) chain. In pro-α1(V), a furin-like proprotein convertase (53) appears to act immediately downstream of the canonical site to cleave the C-propeptide. Thus, the C-propeptides of the α1/α3(V)/α1/α2(XI) subfamily of procollagen chains may all be cleaved by the same, or by similar, furin-like proprotein convertases.

Seven cysteine residues seen at similar positions in the C-propeptides of all previously characterized fibrillar procollagen chains are conserved within the pro-α3(V) C-propeptide or NC1 domain. Sequence alignment also reveals that the pro-α3(V) C-telopeptide is shorter than those of the pro-α1(V), pro-α1(XI), and pro-α2(XI) chains, as is the portion of the pro-α3(V) C-propeptide immediately adjacent to the C-telopeptide. Both regions have previously been noted as areas of relative sequence variability among procollagen chains (74). A potential glycosylation site (NQT) between C-propeptide cysteines 6 and 7, is conserved in both mouse and human pro-α3(V) sequences but is not found in any other fibrillar procollagen C-propeptide. The site may be of specific importance to the structure or function of pro-α3(V) chains.

The α3(V) sequences support the suggestion that basicity of the binding region is a determinant of heparin/heparan sulfate binding in type V/XI collagen chains. While α2(V) and α3(V) chains do not bind heparin under physiological or denaturing conditions (69–71) isolated α1(V) chains do. As evidence that α1(V) chains mediate heparin binding, while α2(V) and α3(V) chains do not (70,71), it is known that triple helical type V collagen trimers bind to heparin with decreasing affinity in the order $\alpha1(V)3>\alpha1(V)_2\alpha2(V)>\alpha1(V)\alpha2(V)\alpha3(V)$. It has been suggested that the low basicity of the region of α2(V) that corresponds to the α1(V) binding site prevents heparin binding. In contrast, high basicity in the corresponding region in type XI chains (69) promotes heparin binding. It can be seen in the sequences that α3(V), like α2(V), has fewer basic residues in this region than do α1(V), α1(XI), or α2(XI). Moreover, α3(V), like α2(V), has more acidic residues in this region than do the other chains, further reducing localized basicity.

EXAMPLE 3

Pro-α3(V) EXPRESSION IN ADULT AND DEVELOPING TISSUES

Patterns of mRNA expression for pro-α3(V) chains were examined and were compared against mRNA expression patterns for pro-α1(V), pro-α2(V), pro-α1(XI) and pro-α2(XI) chains by hybridizing sequence-specific probes, and a ubiquitin control probe, to a multiple tissue expression (MTE) array (Clontech) of dot-blotted poly(A)+ RNA from a variety of adult and fetal human tissues. The MTE array included RNA from whole brain, cerebral cortex, frontal lobe, parietal lobe, occipital lobe, temporal lobe, paracentral gyrus of cerebral cortex, pons, cerebellum left, cerebellum right, corpus callosum, amygdala, caudate nucleus, hippocampus, medulla oblongata, putamen, substantia nigra, accumbens nucleus, thalamus, pituitary gland, spinal cord, heart, aorta, left and right atrium, left and right ventricle, interventricular septum, apex of heart, esophagus, stomach, duodenum, jejunum, ileum, ileocecum, appendix, ascending, transverse and decending colon, rectum, kidney, skeletal muscle, spleen, thymus, peripheral blood leukocyte, lymph node, bone marrow, trachea, lung, placenta, bladder, uterus, prostate, testis, ovary, liver, pancreas, adrenal gland, thyroid gland, salivary gland, mammary gland, leukemia HL-60, HeLa S3, leukemia K-562, leukemia MOLT-4, Burkitt's lymphoma, Raji, Burkitt's lymphoma, Daudi, colorectal adenocarcinoma SW480, lung carcinoma A549, fetal brain, fetal heart, fetal kidney, fetal liver, fetal spleen, fetal thymus and fetal lung. Blots were hybridized to random primed probes in ExpressHyb (Clontech) at 65° C.

The probes were prepared as follows:

α3(V): A 1.6-kb probe corresponding to 3'-UTR and C-propeptide sequences was an EcoRI and FspI fragment of clone HP3-2 (see above).

α1(V): A 1815-bp probe containing mainly triple helical and C-propeptide sequences was an EcoRI fragment of cDNA clone CW32 (27).

α2(V): A a 564-bp probe corresponding to C-propeptide sequences was an EcoRI-HindIII fragment of cDNA clone pBSL18 (43).

α1(XI): A 1,004-bp probe corresponding to C-propeptide and 3'-UTR sequences was amplified from human heart Marathon cDNA with forward primer 5'-TCATCCTAACCAAGGTTGCTCAGG-3' (SEQ ID NO:7) and reverse primer 5'-GAGTCAGCGGAAATTCAGGGACACG-3' (SEQ ID NO:8) using Advantage cDNA polymerase Mix and conditions of 95° C./3 min followed by 35 cycles of 95° C./20 s, 58° C./30 s, 72° C./3 min and final extension at 72° C./7 min. PCR generated probes were cloned into pGEM-T, sequenced to confirm identity, and excised by restriction with SpeI and ApaI.

α2(XI): An 890-bp probe corresponding to C-propeptide and 3'-UTR sequences was amplified by nested PCR. The first round was with primers 5'-AGGCGAGGTGATCCAGCCACTGC-3' (forward; SEQ ID NO:9) and 5'-GCTCTCTAACGGGTAACAGGCTCC-3' (reverse; SEQ ID NO:10) using the same conditions used for PCR amplification of the human α1(XI), except that annealing was at 55° C. The second, nested round was with primers 5'-ATGCAGGAAGATGAGGCCATACC-3' (forward; SEQ ID NO:11) and 5'-GCTCTCTAACGGGTAACAGGCTCC-3' (reverse; SEQ ID NO:12), using 5 ul of a 1/50 dilution of the first round PCR product as template, and conditions of 95° C./3 min followed by 25 cycles of 95° C./20 s, 58° C./30 s, 72° C./3 min and final extension at 72° C./7 min.

Particularly high pro-α3(V) expression was detected in mammary gland, which correlates with the initial isolation of pro-α3(V) sequences as a mouse mammary gland EST and suggests a role for pro-α3(V) chains in this tissue in humans and mice. Relatively high pro-α3(V) mRNA levels were also seen in placenta and uterus, consistent with the results of previous protein studies (12,17–19). In addition, high expression of pro-α3(V) mRNA was found in fetal heart and lung, and moderately high levels were detected in certain structures of adult human heart.

Relatively high levels of pro-α1(V) and pro-α2(V) RNA were found in most of the same human tissues noted for pro-α3(V) expression, which suggests the presence of α1(V)α2(V)α3(V) heterotrimers in these tissues. An exception was adult brain, in which relatively high levels of pro-α3(V) mRNA expression were not matched by high levels of either pro-α1(V) or pro-α2(V) mRNA. These data are consistent with the possibility that pro-α3(V) chains may combine with other procollagen chains or form homotrimers in these regions of adult human brain.

Highest pro-α1(XI) and pro-α2(XI) mRNA levels were seen in trachea, probably reflecting the hyaline cartilage content of this structure. Surprisingly high levels of pro-α1 (XI) and especially high levels of pro-α2(XI) mRNA were also found in structures of adult human brain. While this may suggest heterotrimer formation between pro-α3(V) and one or both type XI procollagen chains in brain, distributions of both type XI procollagen mRNAs in the different brain structures are quite different from that of pro-α3(V) mRNA.

Patterns of mRNA expression for human pro-α3(V) and other fibrillar procollagen chains were further characterized by sequentially hybridizing sequence-specific probes, and a β-actin control probe, to multiple tissue Northern (MTN) blots I, containing approximately 2 μg poly(A)+ RNA per lane from a subset of the tissues examined by dot-blot assay, namely human pancreas, kidney, skeletal muscle, liver, lung, placenta, brain, heart, peripheral leukocytes, colon, small intestine, uterus, testis, prostate, thymus and spleen. Northern blots were washed in 2×SSC, 0.1% SDS at 65° C., followed by 0.1×SSC, 0.1% SDS at 55° C.

The pro-α3(V) expression patterns were generally consistent with those seen by dot-blot, with particularly high levels of expression of a ~6.0-kb band detected in heart, placenta and uterus. As in the dot-blot, pro-α1(V), pro-α2 (V) and pro-α3(V) mRNAs were coexpressed in heart, placenta and uterus. Interestingly, pro-α3(V) mRNA in liver had a somewhat faster mobility (~5.5-kb) than that detected in the other tissues, while the pro-α3(V) mRNA in brain had a considerably faster mobility (~4.2-kb). The nature of the ~4.2-kb transcript in brain is unclear, as the full-length pro-α3(V) coding sequence is 5235-bp and there is no evidence for alternative splicing of the pro-α3(V) N-propeptide.

Spatiotemporal expression patterns of pro-α3(V) mRNA in embryonic murine tissues were examined by hybridizing procollagen-specific probes to a mouse embryo blot containing poly(A)+ RNA from 7, 11, 15, and 17 dpc mouse embryos (Clontech).

Probes for the murine sequences were prepared as follows:

α3(V): A 784 bp probe corresponding to 3'-UTR sequences was amplified from EST IMAGE clone 1366609 with forward primer 5'-TGAAGTTGTG AGGTGGGAAGGAAGCT-3' and reverse primer 5'-GAGCACAGTTCCTTGGTTTATTCT-3' using Advantage cDNA polymerase Mix and conditions of 94° C./3–5 min followed by 30–35 cycles of 94° C./30 s, 55–70° C./30 s, 72° C./3 min and final extension at 72° C./10 min. PCR-generated probes were cloned into pGEM-T, sequenced to confirm identity, and excised by restriction with SpeI and SacII.

α1(V): A 1,206-bp probe corresponding to C-propeptide and 3'-UTR sequences was amplified from 17-dpc mouse embryo Marathon cDNA with forward primer 5'-GGAGAGCTACGTGGATTATGC-3' (SEQ ID NO:13) and reverse primer 5'-CCATCGGAAAGG CACGTGTGG-3' (SEQ ID NO:14), under the conditions noted just above. PCR-generated probes were cloned into pGEM-T, sequenced to confirm identity, and excised by restriction with SpeI and ApaI.

α2(V): A 524-bp probe corresponding to 3'-UTR sequences was amplified from 17-dpc mouse embryo Marathon cDNA with forward primer 5'-CTTCAAGACACCTGCTCTAAGCG-3' (SEQ ID NO:17) and reverse primer 5'-ACATACCCCATC TGTAAGCTACC-3' (SEQ ID NO:18), with the probe gel-purified, direct-sequenced to check identity, and random-primed for blotting.

α1(XI): A 948-bp probe corresponding to C-propeptide and 3'-UTR sequences was amplified from 17-dpc mouse embryo Marathon cDNA with forward primer 5'-GTTTGGATTTGAAGTCGGTCCAGC-3' (SEQ ID NO:19) and reverse primer 5'-TGGCATTACTGA AGCACGCTGAGG-3' (SEQ ID NO:20), under the conditions noted just above. PCR-generated probes were cloned into pGEM-T, sequenced to confirm identity, and excised by restriction with SpeI and ApaI.

α2(XI): A 611-bp α2(XI) Northern blot corresponding to N-propeptide/telopeptide sequences was amplified from 17-dpc mouse embryo Marathon cDNA with forward primer 5'-ATGTGGCTTACCGTG TGGCACG-3' (SEQ ID NO:21) and reverse primer 5'-GCTCTGTGGCTTATGAAGTCTTGC-3' (SEQ ID NO:22), under the conditions noted just above. PCR-generated probes were cloned into pGEM-T, sequenced to confirm identity, and excised by restriction with SpeI and ApaI.

The murine pro-α3(V) probe hybridized to a readily detectable single ~6.3-kb band in the RNA of 7 dpc mid-gastrulation mouse embryos. This mRNA disappears at 11 dpc and was not visible even upon prolonged exposure of the blot, nor was signal for pro-α3(V) RNA detectable at this stage by in situ hybridization of 11 dpc mouse embryos. Pro-α3(V) mRNA reappears at 15 dpc and is further increased in abundance at 17 dpc, during a period of post-organogenesis fetal growth and development.

Among the other fibrillar procollagen mRNAs, strong expression of both pro-α1(V) and pro-α2(V) mRNAs accompany that of pro-α3(V) mRNA at 15 and 17 dpc. Although pro-α2(V) mRNA expression is also strong at 7 dpc, expression of pro-α1(V) is not readily detectable at this stage of development, with low levels of pro-α1(V) mRNA just visible upon prolonged exposure of the blot.

Pro-α1(XI) and pro-α2(XI) mRNAs are also readily detectable at 15 and 17 dpc, but even prolonged exposure of the blot did not reveal detectable levels at 7 and 11 dpc. These results suggest a role for type V, but not type XI collagen chains in mid-gastrulation mouse embryos. The results are also consistent with the possibility that pro-α3(V) chains may exist either as homotrimers or in heterotrimeric combination with pro-α2(V) chains, in the absence of pro-α1(V) chains, at this time. However, the possibility that α3(V) chains are found only in the context of α1(V)α2(V) α3(V) heterotrimers at 7 dpc, despite wide differences in RNA levels for the various chains, has not been excluded.

To determine the distribution of expression of pro-α3(V) during mouse development, and to compare this to the expression domains of other type V/XI procollagen chains, a series of in situ hybridizations were performed on serial sagittal and parasagittal sections of 13.5 dpc and 15.5 dpc mouse embryos using anti-sense, and sense control, riboprobes specific for pro-α3(V), pro-α1(V), pro-α1(XI) and pro-α2(X) sequences. For in situ hybridization, uniform labeling of riboprobes with [35S]UTP, tissue preparation, and hybridization were performed as described (44), except that sections were 5 μm thick and mounted two to six/slide. For histological analysis, sections were prepared and stained with hematoxylin, eosin and alcian blue as described previously (45). Slides were analyzed using light- and dark-field optics of a Zeiss Axiophot 2 microscope.

Probes were prepared as follows using a 17 dpc mouse embryo Marathon cDNA template:

α1(V): A 475-bp probe corresponding to 3'-UTR sequences was amplified using forward primer 5'-TGAGCCCACCGGTCTCCAGAGC-3' (SEQ ID NO:15) and reverse primer 5'-CCATCGGAAAGGC ACGTGTGG-3' (SEQ ID NO:16). Antisense and sense riboprobes were generated by linearizing with NotI and transcribing with T7 two different subclones in which the insert was in opposite orientations.

α3(V): A 1,480-bp probe corresponding to N-propeptide/telopeptide sequences was amplified with forward primer 5'-AGACCAGTCCACATCCCCCTTGGCCT-3' (SEQ ID NO:1; nt 34–59) and reverse primer 5'-CTTTCATGGACAGCTGAGCCTGTTGCA-3' (reverse complement of SEQ ID NO:1; nt 1513–1487). Riboprobes were generated from this template by linearizing with ApaLI and transcribing with polymerase SP6 (antisense) or by linearizing with NotI and transcribing with polymerase T7 (sense).

α1(XI): Antisense and sense riboprobes were generated from the pro-α1(XI) Northern blot probe by linearizing with NotI two subclones of the vector containing the insert in opposite orientations and transcribing with T7.

α2(XI): Antisense and sense riboprobes were generated from the pro-α2(XI) Northern blot probe by linearizing the vector with NotI and transcribing with T7 (antisense) or by linearizing the vector with NcoI and transcribing with SP6 (sense).

At 13.5 dpc pro-α3(V) RNA expression was barely detectable, although pro-α1(V) RNA expression was widely distributed throughout developing mesenchyme and intense pro-α1(XI) and pro-α2(XI) signals were already visible in nascent chondrified cartilaginous elements.

At 15.5 dpc, however, pro-α3(V) expression was readily discernible and the pro-α3(V) expression domain was a subset of that of pro-α1(V). Interestingly, although pro-α1 (V) expression was widely distributed throughout developing connective tissues, with especially high levels of expression seen in the perichondrium associated with cartilaginous primordia of future bones, expression of pro-α3(V) was not detected in perichondrium or other regions of bone primordia, but was instead most readily detectable in the superficial fascia and in the epimysia, or connective tissue sheaths, tracing the outlines of the developing muscles of the anterior chest wall, the cutaneous panniculus carnosus muscle and the developing musculature of the neck. In addition to its expression in epimysium, pro-α3(V) expression was also seen in the connective tissue sheath, or epineureum, of some nerves. Although pro-α3(V) was not expressed in perichondrium, high pro-α3(V) expression was observed closely apposed to the cartilage primordia of future bones in the soft tissue associated with a number of joints, in what appeared to be incipient ligamentous attachments (formation of ligaments and tendons first begins in mouse development, as mesenchymal condensations at 14 dpc, Ref. 75). Pro-α3(V) expression in nascent ligamentous attachments can be seen i) between the cartilage primordia of the bone at the base of the skull and the first two cervical vertebrae C1 (atlas) and C2 (axis), ii) apposed to the cartilage primordium of the exoccipital bone and, iii) between the cartilage primordia of the femoral head and acetabulum of the hip joint. Pro-α3(V) signal was also detectable in forming tendons within the hindlimb.

EXAMPLE 4

MAPPING THE HUMAN COL5A3 AND MOUSE Col5a3 GENES

Chromosomal positions were established for the human COL5A3 and mouse Col5a3 genes that encode the human and murine pro-α3(V) chains, respectively. The human COL5A3 gene was mapped by radiation hybrid mapping (46), using PCR analysis of the Genebridge 4 radiation hybrid panel (Research Genetics). Primers (50 pmol each) were 5'-CTGCTTCAGCAGCTGAGAGTGTCC-3' (forward, SEQ ID NO:3; nt 5309–5332) and 5'-ACCACCTGGCATGGCAAGGTGAGC-3' (reverse, reverse complement of SEQ ID NO:3; nt 5946–5923), in 50-μl reactions with 100 ng template DNA and 2.5 U Taq polymerase (Sigma) at 95° C./5 min followed by 30 cycles of 94° C./30 s, 60° C./45 s, 72° C/2 min and final extension at 72° C./10 min. These conditions amplified a 615-bp product from human genomic DNA template, corresponding to 3'-UTR sequences. Scoring, submitted to the WICGR Mapping Service at the Whitehead Institute/MIT Center for Genome Research, clearly mapped COL5A3 to chromosome 19p, 6.19 cR from WI-8049 and 2.02 cR from WI-7557 (Lod 2.68 relative to most likely). According to the Genome Database, WI-7557 amplifies from gene DNMT1, which has been cytogenetically mapped to 19p13.2 (77). The nearby polymorphic marker should be useful in analyzing linkage with EDS and other disease phenotypes.

The murine Col5a3 gene was mapped by PCR analysis of 94 progeny of the C57BL/6J X *Mus spretus* (BSS) backcross from the Jackson Laboratory (47). Primers (20 pmol each) were 5'-CCTGGCAAGAGGGTGAGTGGTCTTCCA-3' (forward; SEQ ID NO:23) and 5'-GCATCCAGGTTTATG TCAAGAGTGGGCT-3' (reverse; SEQ ID NO:24), in 20-μl reactions with 25 ng template DNA and 0.4 μl Advantage cDNA polymerase mix (Clontech) at 95° C./3 min followed by 30 cycles of 94° C./30 s, 65° C./45 s, 72° C./30 sec and final extension at 72° C./5 min. These conditions amplified 315-bp (C57BL/6J) and 285-bp (*M. spretus*) products, corresponding to Col5a3 intronic sequences with differences in length mostly due to different alleles of a CA polymorphic repeat (25 and 9 CA repeats, respectively). Segregation of these products in the 94 BSS backcross progeny showed linkage of Col5a3 to a region of proximal chromosome 9, which is homologous to human 19p13.2.

Mapping of the human and mouse sequences reported herein to homologous positions in the human and murine genomes, supports the contention that they are human and mouse homologues of the same gene, rather than genes for related, but genetically distinct procollagen chains. No connective tissue or musculoskeletal disorder that might readily arise from defects in the pro-α3(V) chain has yet been mapped to the same chromosomal region as either COL5A3 or Col5a3. However, the highly polymorphic simple sequence (CA) repeat D19S413, with a maximum heterozygosity of 0.78 (78) has, like COL5A3, been mapped to the ~3.6 cM interval between WI-8049 and WI-7557 and, thus, should be of use in the initial analysis of linkage between COL5A3 and disease phenotypes in EDS and other affected families. The observed distribution of pro-α3(V) RNA, and the association of α1(V), α2(V), and α3(V) chains in heterotrimers, suggests the human α3(V) gene COL5A3 as a candidate locus for at least some cases of classical EDS in which the α1(V) and α2(V) genes have been excluded, and for at least some cases of the hypermobility type of EDS.

CITATIONS

All citations mentioned in this patent application are incorporated herein by reference in their entirety as if set forth in full.

1. Birk, D. E., Fitch, J. M., Babiarz, J. P., and Linsenmayer, T. G. (1988) J. Cell Biol. 106, 999–1008

2. Mendler, M., Eich-Bender, S. G., Vaughn, L., Winterhalter, K. H., and Bruckner, P. (1989) J. Cell Biol. 108, 191–197
3. Birk, D. E., Fitch, J. M., Babiarz, J. P., Doane, K. J., and Linsenmayer, T. F. (1990) J. Cell Sci. 95, 649–657
4. Adachi, E., and Hayashi, T. (1996) Connect. Tissue Res. 14, 257–266
5. Andrikopoulos, K., Liu, X., Keene, D. R., Jaenisch, R., and Ramirez, F. (1995) Nature Genet. 9, 31–36
6. Toriello, H. V., Glover, T. W., Takahara, K., Byers, P., Miller, D. E., Higgins, J. V., and Greenspan, D. S. (1996) Nature Genet. 13, 361–365
7. Nicholls, A. C., Oliver, J. E., McCarron, S., Harrison, J. B., Greenspan, D. S., and Pope, F. M. (1996) J. Med. Genet. 33, 940–946
8. Wenstrup, R. J., Langland, G. T., Willing, M. C., D'Souza, V. N., Cole, W. G. (1996) Hum. Mol. Genet. 5, 1733–1736
9. De Paepe, A., Nuytinck, L., Hausser, I., Anton-Lamprecht, I., and Naeyaert, J.-M. (1997) Am. J. Hum. Genet. 60, 547–554
10. Richards, A. J., Martin, S., Nicholls, A. C., Harrison, J. B., Pope, F. M., Burrows, N. P. (1998) J. Med. Genet. 35, 846–848
11. Li, Y., Lacerda, D. A., Warman, M. L., Beier, D. R., Yoshioka, H., Ninomiya, Y., Oxford, J. T., Morris, N. P., Andrikopoulos, K., Ramirez, F., Wardell, B. B., Lifferth, G. D., Teuscher, C., Woodward, S. R., Taylor, B. A., Seegmiller, R. E., and Olsen, B. R. (1995) Cell 80, 423–430
12. Fessler, J. H., and Fessler, L. I. (1987) in Structure and Function of Collagen Types (Mayne, R., and Burgeson, R. E., eds) pp. 81–103, Academic Press, Inc. Orlando, Fla.
13. Fichard, A., Kleman, J.-P., and Ruggiero, F. (1994) Matrix Biol. 14, 515–531
14. Haralson, M. A., Mitchell, W. M., Rhodes, R. K., Kresina, T. F., Gay, R., and Miller, E. J. (1980) Proc. Natl. Acad. Sci. U.S.A. 77, 5206–5210
15. Moradi-Améli, M., Rousseau, J.-C., Kleman, J.-P., Champliaud, M.-F., Boutillon, M.-M., Bernillon, J., Wallach, J., and van der Rest, M. (1994) Eur. J. Biochem. 221, 987–995
16. Kumamoto, C. A., and Fessler, J. H. (1980) Proc. Natl. Acad. Sci U.S.A. 77, 6434–6438
17. Rhodes, R. K., and Miller, E. J. (1981) Collagen Relat. Res. 1, 337–343
18. Niyibizi, C., Fietzek, P. P., and van der Rest, M. (1984) J. Biol. Chem. 259, 14170–14174
19. Abedin, M. Z., Ayad, S., and Weiss, J. B. (1982) Biosci. Rep. 2, 493–502
20. van der Rest, M., and Garrone, R. (1991) FASEB J. 5, 2814–2823
21. Brown, R. A., Shuttleworth, C. A., and Weiss, J. B. (1978) Biochem. Biophys. Res. Commun. 80, 866–872
22. Morris, N. P., and Bächinger, H. P. (1987) J. Biol. Chem. 262, 11345–11350
23. Niyibizi, C., and Eyre, D. R. (1989) FEBS Lett. 242, 314–318
24. Eyre, D., and Wu, J.-J. (1987) in Structure and Function of Collagen Types (Mayne, R., and Burgeson, R. E., eds) pp. 261–281, Academic Press, Inc., Orlando, Fla.
25. Kleman, J.-P., Hartmann, D. J., Ramirez, F., and van der Rest, M. (1992) Eur. J. Biochem. 210, 329–335
26. Mayne, R., Brewton, R. G., Mayne, P. M., and Baker, J. R. (1993) J. Biol. Chem. 268, 9381–9386
27. Greenspan, D. S., Cheng, W., and Hoffman, G. G. (1991) J. Biol. Chem. 266, 24727–24733
28. Takahara, K., Sato, Y., Okazawa, K., Okamoto, N., Noda, A., Yaoi, Y., and Kato, I. (1991) J. Biol. Chem. 266, 13124–13129
29. Bernard, M., Yoshioka, H., Rodriguez, E., van der Rest, M., Kimura, T., Ninomiya, Y., Olsen, B. R., and Ramirez, F. (1988) J. Biol. Chem. 263, 17159–17166
30. Kimura, T., Cheah, K. S. E., Chan, S. D. H., Lui, V. C. H., Mattei, M.-G., van der Rest, M., Ono, K., Solomon, E., Ninomiya, Y., and Olsen, B. R. (1989) J. Biol. Chem. 264, 13910–13916
31. Tsumaki, N., and Kimura, T. (1995) J. Biol. Chem. 270, 2372–2378
32. Weil, D., Bernard, M., Gargano, S., and Ramirez, F. (1987) Nucleic Acids Res. 15, 181–197
33. Zhidkova, N. I., Brewton, R. G., and Mayne, R. (1993) FEBS Lett. 326, 25–28
34. Yoshioka, H., and Ramirez, F. (1990) J. Biol. Chem. 265, 6423–6426
35. Woodbury, D., Benson-Chanda, V., and Ramirez, F. (1989) J. Biol. Chem. 264, 2735–2738
36. Andrikopoulos, K., Suzuki, H. R., Solursh, M., and Ramirez, F. (1992) Dev. Dyn. 195, 113–120
37. Nah, H.-D., Barembaum, M., and Upholt, W. B. (1992) J. Biol. Chem. 267, 22581–22586
38. Yoshioka, H., Iyama, K.-I., Inoguchi, K., Khaleduzzaman, M., Ninomiya, Y., and Ramirez, F. (1995) Dev. Dyn. 204, 41–47
39. Wu, Y.-L., Sumiyoshi, H., Khaleduzzaman, M., Ninomiya, Y., and Yoshioka, H. (1998) Biochim. Biophys. Acta 1397, 275–284
40. Lui, V. C. H., Kong, R. Y. C., Nicholls, J., Cheung, A. N. Y., and Cheah, K. S. E. (1995) Biochem. J. 311, 511–516
41. Sandberg, M. M., Hirvonen, H. E., Elima, K. J., and Vuorio, E. I. (1993) Biochem. J. 294, 595–602
42. Mann, K. (1992) Biol. Chem. Hoppe Seyler 373, 69–75
43. Greenspan, D. S., Hoffman, G. G., and Lee, B.-S. (1989) J. Biol. Chem. 264, 20683–20687
44. Takahara, K., Lyons, G. E., and Greenspan, D. S. (1994) J. Biol. Chem. 269, 32572–32578
45. Scott, I. C., Blitz, I. L., Pappano, W. N., Imamura, Y., Clark, T. G., Steiglitz, B. M., Thomas, C. L., Maas, S. A., Takahara, K., Cho, K. W. Y., and Greenspan, D. S. (1999) Dev. Biol. 213, 283–300
46. Walter, M., Spillet, D., Thomas, P., Weissenbach, J., and Goodfellow, P. (1994) Nat. Genet. 7, 22–28
47. Rowe, L. B., Nadeau, J. H., Turner, R., Frankel, W. N., Letts, V. A., Eppig, J. T., Ko, M. S. H., Thurston, S. J., and Birkenmeier, E. H. (1994) Mamm. Genome 5, 253–274
48. Takahara, K., Hoffman, G. G., and Greenspan, D. S. (1995) Genomics 29, 588–597
49. Vuoristo, M. M., Pihlajamaa, T., Vandenberg, P., Prockop, D. J., and Ala-Kokko, L. (1995) J. Biol. Chem. 270, 22873–22881
50. Neame, P. J., Young, C. N., and Treep, J. T. (1990) J. Biol. Chem. 265, 20401–20408
51. Bork, P. (1992) FEBS Left. 307, 49–54
52. Rousseau, J.-C., Farjanel, J., Boutillon, M.-M., Hartmann, D. J., van der Rest, M., and Moradi-Améli, M. (1996) J. Biol. Chem. 271, 23743–23748
53. Imamura, Y., Steiglitz, B. M., and Greenspan, D. S. (1998) J. Biol. Chem. 273, 27511–27517
54. Linsenmayer, T. F., Gibney, E., Igoe, F., Gordon, M. K., Fitch, J. M., Fessler, L. I., and Birk, D. E. (1993) J. Cell Biol. 121, 1181–1189
55. Bond, J. S., and Beynon, R. J. (1995) Protein Sci. 4, 1247–1261
56. Nakayama, K. (1997) Biochem. J. 327, 625–635
57. Steiner, D. F. (1998) Curr. Opin. Chem. Biol. 2, 31–39
58. Kumamoto, C. A., and Fessler, J. H. (1981) J. Biol. Chem. 256, 7053–7058

59. Broek, D. L., Madri, J., Eikenberry, E. F., and Brodsky, B. (1985) J. Biol. Chem. 260, 555–562
60. Thom, J. R., and Morris, N. P. (1991) J. Biol. Chem. 266, 7262–7269
61. Niyibizi, C., and Eyre, D. R. (1993) Biochim. Biophys. Acta 1203, 304–309
62. Zhidkova, N. I., Justice, S. K., and Mayne, R. (1995) J. Biol. Chem. 270, 9486–9493
63. Oxford, J. T., Doege, K. J., and Morris, N. P. (1995) J. Biol. Chem. 270, 9478–9485
64. Niyibizi, C., and Eyre, D. R. (1994) Eur. J. Biochem. 224, 943–950
65. Wu, J. J-., and Eyre, D. R. (1995) J. Biol. Chem. 270, 18865–18870
66. Ruggiero, F., Comte, J., Cabañas, C., and Garrone, R. (1996) J. Cell Sci. 109, 1865–1874
67. Morris, N. P., Watt, S. L., Davis, J. M., and Bächinger, H. P. (1990) J. Biol. Chem. 265, 10081–10087
68. LeBaron, R. G., Höök, A., Esko, J. D., Gay, S., and Höök, M. (1989) J. Biol. Chem. 264, 7950–7956
69. Yaoi, Y., Hashimoto, K., Koitabashi, H., Takahara, K., Ito, M., and Kato, I. (1990) Biochim. Biophys. Acta 1035, 139–145
70. Delacoux, F., Fichard, A., Geourjon, C., Garrone, R., and Ruggiero, F. (1998) J. Biol. Chem. 273, 15069–15076
71. Mizuno, K., and Hayashi, T. (1996) J. Biochem. 120, 934–939
72. Kessler, E., Takahara, K., Biniaminov, L., Brusel, M., and Greenspan, D. S. (1996) Science 271, 360–362
73. Madri, J., Foellmer, H. G., and Furthmayr, H. (1982) Collagen Relat. Res. 2, 19–29
74. Dion, A. S., and Myers, J. C. (1987) J. Mol. Biol. 193, 127–143
75. Wolfman, N. M., Hattersley, G., Cox, K., Celeste, A. J., Nelson, R., Yamaji, N., Dube, J. L., DiBlasio-Smith, E., Nove, J., Song, J. J., Wozney, J. M., and Rosen, V. (1997) J. Clin. Invest. 100, 321–330
76. Beighton, P., De Paepe, A., Steinmann, B., Tsipouras, P., Wenstrup, R. J. (1998) Am. J. Med. Genet. 77, 31–37
77. Brandriff, B. F., Gordon, L. A., Fertitta, A., Olsen, A. S., Christensen, M., Ashworth, L. K., Nelson, D. O., Carrano, A. V., and Mohrenweiser, H. W. (1994) Genomics 23, 582–591
78. Gyapay, G., Morissette, J., Vignal, A., Dib, C., Fizames, C., Millasseau, P., Marc, S., Bernardi, G., Lathrop, M., and Weissenbach, J. (1994) Nat. Genet. 7, 246–339
79. Beighton, P. (1993) in McKusick's Heritable Disorders of Connective Tissue, 5th ed. (ed. Beighton, P.) pp. 189–251, Mosby-Year Book Inc., St. Louis, Mo.
80. Byers, P. H. (1995) Disorders of collagen biosynthesis and structure in The Metabolic and Molecular Bases of Inherited Disease, 7th ed. (Scriver, C. R., Beaudet, A. L., Sly, W. S. and Valle, D., eds) pp. 4029–4077, McGraw-Hill, New York, N.Y.
81. Jöbsis, G. J., Keizers, H., Vreijling, J. P., de Visser, M., Speer, M. C., Wolterrman, R. A., Baas, F., and Bolhuis, P. A. (1996) Nat. Genet. 14, 113–115
82. Nielsen, H., Engelbrecht, J., Brunak, S., and von Heijne, G. (1997) Protein Eng. 10, 1–6
83. Devereux, J., Haeberli, P., and Smithies, O. (1984) Nucleic Acids Res. 12, 9383–9394

We claim:

1. An isolated polynucleotide selected from the group consisting of a polynucleotide encoding a collagen α3(V) polypeptide, said polynucleotide encoding an amino acid sequence of SEQ ID NO:4, a polynucleotide having 80% identity to the polynucleotide encoding SEQ ID NO:4 over the entire length of the polynucleotide encoding SEQ ID NO:4, a polynucleotide that hybridizes to the polynucleotide encoding SEQ ID NO:4 on overnight incubation at 42° C. in a solution comprising 50% formamide, 5×SSC (150 mM NaCl, 15 mM sodium citrate), 50 mM sodium phosphate (pH 7.6), 5× Denhardt's solution, 10% Dextran Sulfate, and 20 micrograms/ml denatured, sheared salmon sperm DNA, followed by washing the filter in 0.1×SSC at about 65° C. and a complement of any of the polynucleotide.

2. An isolated polynucleotide as claimed in claim 1, wherein the polynucleotide is selected from the group consisting of a polynucleotide that encodes SEQ ID NO:4 and a complement thereof.

3. An expression vector, comprising:

a polynucleotide of claim 1; and a transcriptional control element operably linked to said polynucleotide.

4. An isolated host cell comprising the expression vector of claim 3.

5. An isolated polynucleotide comprising a nucleotide sequence at least 80% identical to SEQ ID NO:3 from nucleotide 87 to nucleotide 5321.

6. The isolated polynucleotide of claim 5, wherein the polynucleotide consists of a nucleotide sequence at least 80% identical to SEQ ID NO:3 from nucleotide 87 to nucleotide 5321.

7. The isolated polynucleotide of claim 6, wherein the polynucleotide consists of SEQ ID NO:3 from nucleotide 87 to nucleotide 5321.

8. An isolated polynucleotide having a nucleotide sequence at least 90% identical to SEQ ID NO:3.

9. The isolated polynucleotide of claim 8, wherein the nucleotide sequence is at least 95% identical to SEQ ID NO:3.

* * * * *

SEQUENCE LISTING

```
<160> NUMBER OF SEQ ID NOS:  24

<210> SEQ ID NO 1
<211> LENGTH: 6109
<212> TYPE: DNA
<213> ORGANISM: Mus musculus
<220> FEATURE:
<221> NAME/KEY: CDS
<222> LOCATION: (82)..(5298)

<400> SEQUENCE: 1

gcctccggct gtccagagtg actgctccca ggaagaccag tccacatccc ccttggcctt      60

ggtgcaccag gccccgctgg g atg aga agc tgc cgg aga ctg gat cag ctt       111
                        Met Arg Ser Cys Arg Arg Leu Asp Gln Leu
                          1               5                  10

cag gcc ggc ctc tgc ctg ctc ctg gcc tcc ctg cag ctc gtg tcc tgg       159
Gln Ala Gly Leu Cys Leu Leu Leu Ala Ser Leu Gln Leu Val Ser Trp
                15                  20                  25

acg ctg gct gca gaa cct gtg gac gta ctg gaa gcc tgg ggt gtg cat       207
Thr Leu Ala Ala Glu Pro Val Asp Val Leu Glu Ala Trp Gly Val His
            30                  35                  40

aga gac cag gct ggg gtg gct gaa ggg cct ggc ttc tgc ccc ctg agg       255
Arg Asp Gln Ala Gly Val Ala Glu Gly Pro Gly Phe Cys Pro Leu Arg
        45                  50                  55

att cca cag ggt gac cga gca ttc agg gtg ggc aag tcc agc ctt ctc       303
Ile Pro Gln Gly Asp Arg Ala Phe Arg Val Gly Lys Ser Ser Leu Leu
    60                  65                  70

agt gtc ccc acg tgg cag ctc ttc cca gat ggg cat ttt cct gag aac       351
Ser Val Pro Thr Trp Gln Leu Phe Pro Asp Gly His Phe Pro Glu Asn
```

-continued

```
 75                  80                  85                  90

ttt tct gtg ctg ctc aca ctg agg gcc cag cca gcc aat cag tct gtc      399
Phe Ser Val Leu Leu Thr Leu Arg Ala Gln Pro Ala Asn Gln Ser Val
                 95                 100                 105

ctt ctg tct att tat gat gag aag ggt gtc cgg cag ctg ggg ctg gca      447
Leu Leu Ser Ile Tyr Asp Glu Lys Gly Val Arg Gln Leu Gly Leu Ala
             110                 115                 120

ctg ggg cca gct ctg ggc ctc ctt ggt gac tcc ttc agg ccc ctc ccc      495
Leu Gly Pro Ala Leu Gly Leu Leu Gly Asp Ser Phe Arg Pro Leu Pro
         125                 130                 135

aag caa gtc aac att atg gat ggc agg tgg cac cgt gtg gca gtc agc      543
Lys Gln Val Asn Ile Met Asp Gly Arg Trp His Arg Val Ala Val Ser
     140                 145                 150

atc agt ggt aac aag gtg acc ctg gtg gtt gac tgt gaa ccg cag ccc      591
Ile Ser Gly Asn Lys Val Thr Leu Val Val Asp Cys Glu Pro Gln Pro
155                 160                 165                 170

cca aca ttt ggt cag ggg cct cgg ttt ata agt aca gct gga ctc act      639
Pro Thr Phe Gly Gln Gly Pro Arg Phe Ile Ser Thr Ala Gly Leu Thr
                 175                 180                 185

gtg atg gga acc cag gac acc agg gaa gag tct ttt gag gga gac atc      687
Val Met Gly Thr Gln Asp Thr Arg Glu Glu Ser Phe Glu Gly Asp Ile
             190                 195                 200

cag gag ctg ctg tta att cca gac cct cag gct gcc ttc cag gcc tgt      735
Gln Glu Leu Leu Leu Ile Pro Asp Pro Gln Ala Ala Phe Gln Ala Cys
         205                 210                 215

gag agc tac ctc cct ggt tgt gaa acc ctc gat tcc aca acc aca ggg      783
Glu Ser Tyr Leu Pro Gly Cys Glu Thr Leu Asp Ser Thr Thr Thr Gly
     220                 225                 230

gcc ccc aaa gac gat gaa cca gaa acc cct gcc cct cgt cgt cga aag      831
Ala Pro Lys Asp Asp Glu Pro Glu Thr Pro Ala Pro Arg Arg Arg Lys
235                 240                 245                 250

ggc aaa ggg aag aaa aaa ggg cgg ggt cga aag ggc aag gga aga aag      879
Gly Lys Gly Lys Lys Lys Gly Arg Gly Arg Lys Gly Lys Gly Arg Lys
                 255                 260                 265

aaa aac aag gag acc tca gag ctg agt ccg acc cct ggt gcc cct gag      927
Lys Asn Lys Glu Thr Ser Glu Leu Ser Pro Thr Pro Gly Ala Pro Glu
             270                 275                 280

aac cag acc tcc ctc cac atc cct gag aca gag aag aca gtt ccc cac      975
Asn Gln Thr Ser Leu His Ile Pro Glu Thr Glu Lys Thr Val Pro His
         285                 290                 295

ctg cct ctg act ccc aca cct ctg gcc atc acc acc act gtc acg att     1023
Leu Pro Leu Thr Pro Thr Pro Leu Ala Ile Thr Thr Thr Val Thr Ile
     300                 305                 310

gga caa aat gcc aca gtc tcg cag ggg ttg gac tcc ggt act gaa acc     1071
Gly Gln Asn Ala Thr Val Ser Gln Gly Leu Asp Ser Gly Thr Glu Thr
315                 320                 325                 330

gag cag acg act cca gag gtg gac tct act gag gag ggt gaa gga ggt     1119
Glu Gln Thr Thr Pro Glu Val Asp Ser Thr Glu Glu Gly Glu Gly Gly
                 335                 340                 345

ggc ccc acc atg ggc ccc aag ttc cgg gca gca gag cag tcc tta cag     1167
Gly Pro Thr Met Gly Pro Lys Phe Arg Ala Ala Glu Gln Ser Leu Gln
             350                 355                 360

act gag ttc cag atc ttt cct ggt gct gga gaa aag gga gcg aaa gga     1215
Thr Glu Phe Gln Ile Phe Pro Gly Ala Gly Glu Lys Gly Ala Lys Gly
         365                 370                 375

gag cct gcg aca gta gag cag gga cag cag ttt gag ggg cct gca gga     1263
Glu Pro Ala Thr Val Glu Gln Gly Gln Gln Phe Glu Gly Pro Ala Gly
     380                 385                 390

gct cca gga ccc cgg gga ata tct ggt cct tca ggc cct cct ggg cct     1311
```

-continued

```
Ala Pro Gly Pro Arg Gly Ile Ser Gly Pro Ser Gly Pro Pro Gly Pro
395                 400                 405                 410

ccg ggc ttc cct ggg gac cgt ggt cta ccg ggt cct gcc ggc ctc cca      1359
Pro Gly Phe Pro Gly Asp Arg Gly Leu Pro Gly Pro Ala Gly Leu Pro
                415                 420                 425

gga atc cca ggc atc gat gga gcc cgg ggc ctg ccg ggc aca gtg att      1407
Gly Ile Pro Gly Ile Asp Gly Ala Arg Gly Leu Pro Gly Thr Val Ile
            430                 435                 440

atg atg ccg ttc cat ttt gca agc agc tcg atg aag gga ccc cca gtg      1455
Met Met Pro Phe His Phe Ala Ser Ser Ser Met Lys Gly Pro Pro Val
        445                 450                 455

tcc ttc cag cag gcc cag gcc cag gca gta ttg caa cag gct cag ctg      1503
Ser Phe Gln Gln Ala Gln Ala Gln Ala Val Leu Gln Gln Ala Gln Leu
    460                 465                 470

tcc atg aaa ggg ccc cct ggt cca gta ggg ctc act ggg cgc cca ggc      1551
Ser Met Lys Gly Pro Pro Gly Pro Val Gly Leu Thr Gly Arg Pro Gly
475                 480                 485                 490

cct gtg ggc ctc cct gga tat cca ggt ctg aaa ggt gaa ctg gga gaa      1599
Pro Val Gly Leu Pro Gly Tyr Pro Gly Leu Lys Gly Glu Leu Gly Glu
                495                 500                 505

gtg ggg cca cag ggc ccc cga gga tta cag ggc cct cct ggg cct cct      1647
Val Gly Pro Gln Gly Pro Arg Gly Leu Gln Gly Pro Pro Gly Pro Pro
            510                 515                 520

gga cgg gaa ggc aag aca ggc cga gct gga gca gat ggg gct cgg ggg      1695
Gly Arg Glu Gly Lys Thr Gly Arg Ala Gly Ala Asp Gly Ala Arg Gly
        525                 530                 535

ctc ccg gga gac aca gga cct aag ggt gac agg ggc ttt gat ggc ctg      1743
Leu Pro Gly Asp Thr Gly Pro Lys Gly Asp Arg Gly Phe Asp Gly Leu
    540                 545                 550

ccc ggg ctg cct ggt gag aag ggc caa agg ggt gac ttt gga cga gta      1791
Pro Gly Leu Pro Gly Glu Lys Gly Gln Arg Gly Asp Phe Gly Arg Val
555                 560                 565                 570

ggg caa cct ggt ccc cca gga gag gat ggt gta aag ggc ctg cag gga      1839
Gly Gln Pro Gly Pro Pro Gly Glu Asp Gly Val Lys Gly Leu Gln Gly
                575                 580                 585

cct cca ggg ccc act ggc cag gct gga gag ccg ggt ccc cga ggt ctg      1887
Pro Pro Gly Pro Thr Gly Gln Ala Gly Glu Pro Gly Pro Arg Gly Leu
            590                 595                 600

att ggc ccc aga ggt ctc cca ggt ccc cta gga cgc ccg ggt gtg aca      1935
Ile Gly Pro Arg Gly Leu Pro Gly Pro Leu Gly Arg Pro Gly Val Thr
        605                 610                 615

ggg agt gat ggc gca cca ggg gcc aaa ggc aac gtg ggt cct cct gga      1983
Gly Ser Asp Gly Ala Pro Gly Ala Lys Gly Asn Val Gly Pro Pro Gly
    620                 625                 630

gaa cca gga ccc cca gga cag caa gga aac cac ggc tcc cag gga att      2031
Glu Pro Gly Pro Pro Gly Gln Gln Gly Asn His Gly Ser Gln Gly Ile
635                 640                 645                 650

cca ggc ccc cag ggg ccc att ggc act ccc ggg gaa aag ggt ccc cct      2079
Pro Gly Pro Gln Gly Pro Ile Gly Thr Pro Gly Glu Lys Gly Pro Pro
                655                 660                 665

gga aac ccc gga att cca ggt gtc cca gga tct gag ggc ccc ccg ggc      2127
Gly Asn Pro Gly Ile Pro Gly Val Pro Gly Ser Glu Gly Pro Pro Gly
            670                 675                 680

cac cca ggc cac gag ggt ccc aca gga gaa aaa ggg gct cag ggc cca      2175
His Pro Gly His Glu Gly Pro Thr Gly Glu Lys Gly Ala Gln Gly Pro
        685                 690                 695

cca gga tca gca ggc cct cgg ggc tat cct gga ctt cgt ggt gtg aag      2223
Pro Gly Ser Ala Gly Pro Arg Gly Tyr Pro Gly Leu Arg Gly Val Lys
    700                 705                 710
```

-continued

```
ggt acc tct ggt aac cgg ggt ctc caa ggc gag aaa gga gaa agg gga      2271
Gly Thr Ser Gly Asn Arg Gly Leu Gln Gly Glu Lys Gly Glu Arg Gly
715                 720                 725                 730

gag gat ggc ttt cct ggc ttc aag ggt gat gag gga cca aaa ggc gac      2319
Glu Asp Gly Phe Pro Gly Phe Lys Gly Asp Glu Gly Pro Lys Gly Asp
                735                 740                 745

cgg gga aac ccc gga ccc cca ggt ccc aga gga gag gat ggt cca gaa      2367
Arg Gly Asn Pro Gly Pro Pro Gly Pro Arg Gly Glu Asp Gly Pro Glu
            750                 755                 760

gga caa aag ggg cct ggg gga ctg cct ggt gat gag ggt cct cca gga      2415
Gly Gln Lys Gly Pro Gly Gly Leu Pro Gly Asp Glu Gly Pro Pro Gly
        765                 770                 775

gca gca ggg gag aag ggc aag ctt ggg gtg cca ggt ctc cca ggt tat      2463
Ala Ala Gly Glu Lys Gly Lys Leu Gly Val Pro Gly Leu Pro Gly Tyr
    780                 785                 790

cca gga cgc cca gga cct aag gga tct att gga ttt cct gga ccc ttg      2511
Pro Gly Arg Pro Gly Pro Lys Gly Ser Ile Gly Phe Pro Gly Pro Leu
795                 800                 805                 810

gga cca ctg ggg gag aaa ggc aag cgg ggc aaa gca gga cag cca gga      2559
Gly Pro Leu Gly Glu Lys Gly Lys Arg Gly Lys Ala Gly Gln Pro Gly
                815                 820                 825

gag gaa gga gaa cgc ggc aca ccg ggc acc cga gga gac agg gga cag      2607
Glu Glu Gly Glu Arg Gly Thr Pro Gly Thr Arg Gly Asp Arg Gly Gln
            830                 835                 840

ccg ggg gcc aca ggc cag cct ggc ccc aag ggt gac gtg ggc cag aat      2655
Pro Gly Ala Thr Gly Gln Pro Gly Pro Lys Gly Asp Val Gly Gln Asn
        845                 850                 855

ggg tct cct ggg ccc cct ggg gaa aag ggt cta ccc ggt ctt caa ggc      2703
Gly Ser Pro Gly Pro Pro Gly Glu Lys Gly Leu Pro Gly Leu Gln Gly
    860                 865                 870

cca cca gga ttc ccc gga cca aaa ggc ccc ccg ggt cct cag ggg aaa      2751
Pro Pro Gly Phe Pro Gly Pro Lys Gly Pro Pro Gly Pro Gln Gly Lys
875                 880                 885                 890

gac ggg ata tct ggg cac cct gga caa aga gga gaa ttg ggc ttc caa      2799
Asp Gly Ile Ser Gly His Pro Gly Gln Arg Gly Glu Leu Gly Phe Gln
                895                 900                 905

ggt ctg aca ggc ccc cct gga cca gct ggc gtc ctt ggt cct cag gga      2847
Gly Leu Thr Gly Pro Pro Gly Pro Ala Gly Val Leu Gly Pro Gln Gly
            910                 915                 920

aag gta ggg gac gtg ggg cct cta ggc gag aga ggc ccc cca ggg cct      2895
Lys Val Gly Asp Val Gly Pro Leu Gly Glu Arg Gly Pro Pro Gly Pro
        925                 930                 935

cct gga cct cct ggt gaa caa ggt ctg cca ggc ata gaa ggc aga gaa      2943
Pro Gly Pro Pro Gly Glu Gln Gly Leu Pro Gly Ile Glu Gly Arg Glu
    940                 945                 950

ggg gcc aag ggt gag cta gga ccc ctg ggg tcc gtc ggg aag gag ggg      2991
Gly Ala Lys Gly Glu Leu Gly Pro Leu Gly Ser Val Gly Lys Glu Gly
955                 960                 965                 970

cca cct ggg ccc agg ggc ttc cct ggc ccc caa gga gcc ccc gga gac      3039
Pro Pro Gly Pro Arg Gly Phe Pro Gly Pro Gln Gly Ala Pro Gly Asp
                975                 980                 985

cca gga ccc att ggt ttg aag ggt gac aaa ggt ccc cca ggc cct gtt      3087
Pro Gly Pro Ile Gly Leu Lys Gly Asp Lys Gly Pro Pro Gly Pro Val
            990                 995                1000

ggg gca aat ggc tcc ccg gga gag cgt ggt cct gta ggc ccc tct ggt      3135
Gly Ala Asn Gly Ser Pro Gly Glu Arg Gly Pro Val Gly Pro Ser Gly
       1005                1010                1015

ggc att ggg ctt cct ggc cag agt gga ggg caa ggc cct att ggt cct      3183
Gly Ile Gly Leu Pro Gly Gln Ser Gly Gly Gln Gly Pro Ile Gly Pro
   1020                1025                1030
```

-continued

```
gct ggc gag aag ggg tcc ccg gga gaa cgg ggt act cct ggt cct act      3231
Ala Gly Glu Lys Gly Ser Pro Gly Glu Arg Gly Thr Pro Gly Pro Thr
1035                1040                1045                1050

ggc aaa gat ggt att cca gga ccc ccg ggg ctt cag ggc ccc tct gga      3279
Gly Lys Asp Gly Ile Pro Gly Pro Pro Gly Leu Gln Gly Pro Ser Gly
                1055                1060                1065

gct gcg ggg cct tct ggg gaa gaa gga gac aag ggg gaa gta ggg atg      3327
Ala Ala Gly Pro Ser Gly Glu Glu Gly Asp Lys Gly Glu Val Gly Met
            1070                1075                1080

cct ggt cac aaa gga agc aaa ggg gat aaa gga gat gca ggc cca cct      3375
Pro Gly His Lys Gly Ser Lys Gly Asp Lys Gly Asp Ala Gly Pro Pro
        1085                1090                1095

gga cca aca gga ata aga ggt cca gca ggc cat tca ggc ctc ccg ggt      3423
Gly Pro Thr Gly Ile Arg Gly Pro Ala Gly His Ser Gly Leu Pro Gly
    1100                1105                1110

gct gat ggc gct cag ggt cgc cgg gga ccc cct ggc ctc ttc ggg cag      3471
Ala Asp Gly Ala Gln Gly Arg Arg Gly Pro Pro Gly Leu Phe Gly Gln
1115                1120                1125                1130

aag ggg gat gac gga gtt cga ggc ttt gta ggt gta att ggt cct cca      3519
Lys Gly Asp Asp Gly Val Arg Gly Phe Val Gly Val Ile Gly Pro Pro
                1135                1140                1145

ggt ctg cag ggg ctg ccg ggt cct ccg ggg gag aag ggc gag gtt gga      3567
Gly Leu Gln Gly Leu Pro Gly Pro Pro Gly Glu Lys Gly Glu Val Gly
            1150                1155                1160

gac gta gga tcc atg ggt cca cat gga gct cca ggc cct cgg ggt ccc      3615
Asp Val Gly Ser Met Gly Pro His Gly Ala Pro Gly Pro Arg Gly Pro
        1165                1170                1175

cct ggg ccc agt gga tca gag ggc ccc cca ggt ctg cct gga gga gta      3663
Pro Gly Pro Ser Gly Ser Glu Gly Pro Pro Gly Leu Pro Gly Gly Val
    1180                1185                1190

gga cag cct ggt gct gtg ggc gag aag ggt gag cca ggg gat gct gga      3711
Gly Gln Pro Gly Ala Val Gly Glu Lys Gly Glu Pro Gly Asp Ala Gly
1195                1200                1205                1210

gac gcc gga ccc cca gga att ccc ggc atc cct ggg ccc aaa ggt gaa      3759
Asp Ala Gly Pro Pro Gly Ile Pro Gly Ile Pro Gly Pro Lys Gly Glu
                1215                1220                1225

att ggt gaa aag ggg gat tcg ggt cca tca ggg gct gct ggt ccc cca      3807
Ile Gly Glu Lys Gly Asp Ser Gly Pro Ser Gly Ala Ala Gly Pro Pro
            1230                1235                1240

ggc aag aaa gga ccc cca gga gag gac ggc tct aag ggg aac atg ggt      3855
Gly Lys Lys Gly Pro Pro Gly Glu Asp Gly Ser Lys Gly Asn Met Gly
        1245                1250                1255

ccc aca gga ctc cct gga gat cta ggg ccc cca gga gac cct gga gtt      3903
Pro Thr Gly Leu Pro Gly Asp Leu Gly Pro Pro Gly Asp Pro Gly Val
    1260                1265                1270

ccg ggt att gat ggc atc cca ggg gag aag gga aat gct ggt gat att      3951
Pro Gly Ile Asp Gly Ile Pro Gly Glu Lys Gly Asn Ala Gly Asp Ile
1275                1280                1285                1290

ggg gga ccg ggg cca cct gga gct tcc ggg gaa cct ggt gcc cgt ggc      3999
Gly Gly Pro Gly Pro Pro Gly Ala Ser Gly Glu Pro Gly Ala Arg Gly
                1295                1300                1305

ctc cct ggc aag agg ggt tcc cct ggc cgc atg ggt cca gaa gga aga      4047
Leu Pro Gly Lys Arg Gly Ser Pro Gly Arg Met Gly Pro Glu Gly Arg
            1310                1315                1320

gag ggc gag aaa ggc gcc aag gga gat gct ggt cct gat gga ccc cca      4095
Glu Gly Glu Lys Gly Ala Lys Gly Asp Ala Gly Pro Asp Gly Pro Pro
        1325                1330                1335

ggc agg aca ggc ccc att ggg gct cga ggg ccc cct gga cga att ggg      4143
Gly Arg Thr Gly Pro Ile Gly Ala Arg Gly Pro Pro Gly Arg Ile Gly
```

-continued

```
 1340                1345                1350

cct gat ggt ctt cca ggg atc cct ggt cct gtg ggt gaa cca ggt ctc     4191
Pro Asp Gly Leu Pro Gly Ile Pro Gly Pro Val Gly Glu Pro Gly Leu
1355                1360                1365                1370

ctg gga cct cct ggg cta atc ggc cct cca ggg ccc ctg ggc cca cct     4239
Leu Gly Pro Pro Gly Leu Ile Gly Pro Pro Gly Pro Leu Gly Pro Pro
                1375                1380                1385

ggc ctc cct ggc ctg aag gga gat gct ggc ccc aag ggg gag aag ggc     4287
Gly Leu Pro Gly Leu Lys Gly Asp Ala Gly Pro Lys Gly Glu Lys Gly
            1390                1395                1400

cac att ggg cta ata ggc ctc att ggt ccc cca ggg gag gcc ggt gag     4335
His Ile Gly Leu Ile Gly Leu Ile Gly Pro Pro Gly Glu Ala Gly Glu
        1405                1410                1415

aaa ggc gat cag ggg ttg cca ggt gtg cag ggc ccc cca ggc ctt cag     4383
Lys Gly Asp Gln Gly Leu Pro Gly Val Gln Gly Pro Pro Gly Leu Gln
    1420                1425                1430

gga gac cct ggt ctc cct ggt cct gtt ggc tcg tta ggt cac cct ggg     4431
Gly Asp Pro Gly Leu Pro Gly Pro Val Gly Ser Leu Gly His Pro Gly
1435                1440                1445                1450

ccc cca ggt gtg gtg ggc cct ctg gga cag aag ggc tcc aaa ggg tcc     4479
Pro Pro Gly Val Val Gly Pro Leu Gly Gln Lys Gly Ser Lys Gly Ser
                1455                1460                1465

ccg gga tct ctt ggt cct cgt gga gac cct gga cca gcg ggt cct cct     4527
Pro Gly Ser Leu Gly Pro Arg Gly Asp Pro Gly Pro Ala Gly Pro Pro
            1470                1475                1480

ggt ccc ccg ggt tct ccg gct gag gtg cat ggc ctg cgc agg cgc cga     4575
Gly Pro Pro Gly Ser Pro Ala Glu Val His Gly Leu Arg Arg Arg Arg
        1485                1490                1495

tct gtg acg gac acc ctg gaa ggt ggc ctg gag gag gtg atg gcc tca     4623
Ser Val Thr Asp Thr Leu Glu Gly Gly Leu Glu Glu Val Met Ala Ser
    1500                1505                1510

ctg aat tca ctg agc ttg gag ctg cag cag ttg cag aga cct ctg ggc     4671
Leu Asn Ser Leu Ser Leu Glu Leu Gln Gln Leu Gln Arg Pro Leu Gly
1515                1520                1525                1530

aca gcc gag agc cca ggc ctc atg tgc cga gag ctt cac cgc gac cac     4719
Thr Ala Glu Ser Pro Gly Leu Met Cys Arg Glu Leu His Arg Asp His
                1535                1540                1545

cca cac ctg ccc gat gga gag tac tgg att gac ccc aat cag ggc tgt     4767
Pro His Leu Pro Asp Gly Glu Tyr Trp Ile Asp Pro Asn Gln Gly Cys
            1550                1555                1560

gca cgt gac gcc ttc aag gtt ttc tgc aac ttc acg gca gga ggt gag     4815
Ala Arg Asp Ala Phe Lys Val Phe Cys Asn Phe Thr Ala Gly Gly Glu
        1565                1570                1575

acc tgt ctc tat cca gac aag aag ttt gag acg gtg aaa ctg gcc tcg     4863
Thr Cys Leu Tyr Pro Asp Lys Lys Phe Glu Thr Val Lys Leu Ala Ser
    1580                1585                1590

tgg tcc cga gag aag cct gga ggc tgg tac agc acc ttc cgc cga ggg     4911
Trp Ser Arg Glu Lys Pro Gly Gly Trp Tyr Ser Thr Phe Arg Arg Gly
1595                1600                1605                1610

aag aag ttc tcc tat gtg gat gct gat ggc tcc ccg gtg aat gtg gtc     4959
Lys Lys Phe Ser Tyr Val Asp Ala Asp Gly Ser Pro Val Asn Val Val
                1615                1620                1625

cag ttg acc ttc ctg aag ttg ttg agt gct gca gcc cat cag agg ttc     5007
Gln Leu Thr Phe Leu Lys Leu Leu Ser Ala Ala Ala His Gln Arg Phe
            1630                1635                1640

act tac atc tgc cag aac tcg gtg gca tgg ctg gat gaa gct gcg ggt     5055
Thr Tyr Ile Cys Gln Asn Ser Val Ala Trp Leu Asp Glu Ala Ala Gly
        1645                1650                1655

gac cac agg cac tcc atc cgc ttc caa ggg acc aac tgg gaa gag ttg     5103
```

-continued

```
Asp His Arg His Ser Ile Arg Phe Gln Gly Thr Asn Trp Glu Glu Leu
   1660                1665                1670

tcc ttc aac cag aca aca gca gct acc atc aag gtc tcc cat gat ggc     5151
Ser Phe Asn Gln Thr Thr Ala Ala Thr Ile Lys Val Ser His Asp Gly
1675                1680                1685                1690

tgt cgg gtc cgg aag gga cag gcg aag acc ctc ttt gaa ttc agc tct     5199
Cys Arg Val Arg Lys Gly Gln Ala Lys Thr Leu Phe Glu Phe Ser Ser
               1695                1700                1705

tct gtg ggt ttc ctg cct ctg tgg gat gtg gct gcc tct gac ttt ggt     5247
Ser Val Gly Phe Leu Pro Leu Trp Asp Val Ala Ala Ser Asp Phe Gly
           1710                1715                1720

cag acg aac caa aag ttt ggg ttt gaa ctc ggc tcc atc tgc ttt agc     5295
Gln Thr Asn Gln Lys Phe Gly Phe Glu Leu Gly Ser Ile Cys Phe Ser
       1725                1730                1735

agc tgaagttgtg aggtgggaag gaagctgaag ggagccccac atgggctcct          5348
Ser

tggtgctgag gctctgaggc cattctgttt atccccaggg actccagatc cagggtcacg   5408

tgactctgac tattctttct cccttgtagg gggagagtgt ggagagccca gctccctctg   5468

tctgttcacc ccaggtggta tacccagttg tctgctagct ccccccctcca tccaactgtc   5528

cattgtccac ctcaccccca gacctccatg cagtagactt ttaactcaga gctggtgaag   5588

ccccacccct gcctctccac ccctccacca ggccttttgg tgctattcct ttccatagtt   5648

gagcactgga tacctcctga tccctgcctg ggacccttcc ctcgcatact tcttctttct   5708

ttgagtaaaa gaagtaaagc aagatcaaag ggggcgccct ccctgagctg cgccttcctt   5768

ctgcttcctt gacccagtgc tgcacaatct cctctcccta ctctgcccca ctcctgtgcc   5828

cccaagcctt caggggacca agatgttggg cataaatcag gatcctacat ggtgctgccc   5888

tgctcataac tgggaactgt atgaaagggg gaatgaatgg tctgtggtct atttaatttg   5948

cttccttctg aaggaagtct ggggtacggt gagagattcc agaaggatct gtaccctccc   6008

ttacctacgc ggctctcctc cccaggacac agggcaaaat cgccatctca agaataaacc   6068

aaggaactgt gctcttctaa aaaaaaaaaa aaaaaaaaaa a                       6109


<210> SEQ ID NO 2
<211> LENGTH: 1739
<212> TYPE: PRT
<213> ORGANISM: Mus musculus

<400> SEQUENCE: 2

Met Arg Ser Cys Arg Arg Leu Asp Gln Leu Gln Ala Gly Leu Cys Leu
  1               5                  10                  15

Leu Leu Ala Ser Leu Gln Leu Val Ser Trp Thr Leu Ala Ala Glu Pro
             20                  25                  30

Val Asp Val Leu Glu Ala Trp Gly Val His Arg Asp Gln Ala Gly Val
         35                  40                  45

Ala Glu Gly Pro Gly Phe Cys Pro Leu Arg Ile Pro Gln Gly Asp Arg
     50                  55                  60

Ala Phe Arg Val Gly Lys Ser Ser Leu Leu Ser Val Pro Thr Trp Gln
 65                  70                  75                  80

Leu Phe Pro Asp Gly His Phe Pro Glu Asn Phe Ser Val Leu Leu Thr
                 85                  90                  95

Leu Arg Ala Gln Pro Ala Asn Gln Ser Val Leu Leu Ser Ile Tyr Asp
            100                 105                 110

Glu Lys Gly Val Arg Gln Leu Gly Leu Ala Leu Gly Pro Ala Leu Gly
        115                 120                 125
```

```
Leu Leu Gly Asp Ser Phe Arg Pro Leu Pro Lys Gln Val Asn Ile Met
    130                 135                 140

Asp Gly Arg Trp His Arg Val Ala Val Ser Ile Ser Gly Asn Lys Val
145                 150                 155                 160

Thr Leu Val Val Asp Cys Glu Pro Gln Pro Pro Thr Phe Gly Gln Gly
                165                 170                 175

Pro Arg Phe Ile Ser Thr Ala Gly Leu Thr Val Met Gly Thr Gln Asp
            180                 185                 190

Thr Arg Glu Glu Ser Phe Glu Gly Asp Ile Gln Glu Leu Leu Leu Ile
        195                 200                 205

Pro Asp Pro Gln Ala Ala Phe Gln Ala Cys Glu Ser Tyr Leu Pro Gly
    210                 215                 220

Cys Glu Thr Leu Asp Ser Thr Thr Thr Gly Ala Pro Lys Asp Asp Glu
225                 230                 235                 240

Pro Glu Thr Pro Ala Pro Arg Arg Arg Lys Gly Lys Gly Lys Lys Lys
                245                 250                 255

Gly Arg Gly Arg Lys Gly Lys Gly Arg Lys Lys Asn Lys Glu Thr Ser
            260                 265                 270

Glu Leu Ser Pro Thr Pro Gly Ala Pro Glu Asn Gln Thr Ser Leu His
        275                 280                 285

Ile Pro Glu Thr Glu Lys Thr Val Pro His Leu Pro Leu Thr Pro Thr
    290                 295                 300

Pro Leu Ala Ile Thr Thr Thr Val Thr Ile Gly Gln Asn Ala Thr Val
305                 310                 315                 320

Ser Gln Gly Leu Asp Ser Gly Thr Glu Thr Glu Gln Thr Thr Pro Glu
                325                 330                 335

Val Asp Ser Thr Glu Glu Gly Glu Gly Gly Gly Pro Thr Met Gly Pro
            340                 345                 350

Lys Phe Arg Ala Ala Glu Gln Ser Leu Gln Thr Glu Phe Gln Ile Phe
        355                 360                 365

Pro Gly Ala Gly Glu Lys Gly Ala Lys Gly Glu Pro Ala Thr Val Glu
    370                 375                 380

Gln Gly Gln Gln Phe Glu Gly Pro Ala Gly Ala Pro Gly Pro Arg Gly
385                 390                 395                 400

Ile Ser Gly Pro Ser Gly Pro Pro Gly Pro Pro Gly Phe Pro Gly Asp
                405                 410                 415

Arg Gly Leu Pro Gly Pro Ala Gly Leu Pro Gly Ile Pro Gly Ile Asp
            420                 425                 430

Gly Ala Arg Gly Leu Pro Gly Thr Val Ile Met Met Pro Phe His Phe
        435                 440                 445

Ala Ser Ser Ser Met Lys Gly Pro Pro Val Ser Phe Gln Gln Ala Gln
    450                 455                 460

Ala Gln Ala Val Leu Gln Gln Ala Gln Leu Ser Met Lys Gly Pro Pro
465                 470                 475                 480

Gly Pro Val Gly Leu Thr Gly Arg Pro Gly Pro Val Gly Leu Pro Gly
                485                 490                 495

Tyr Pro Gly Leu Lys Gly Glu Leu Gly Glu Val Gly Pro Gln Gly Pro
            500                 505                 510

Arg Gly Leu Gln Gly Pro Pro Gly Pro Pro Gly Arg Glu Gly Lys Thr
        515                 520                 525

Gly Arg Ala Gly Ala Asp Gly Ala Arg Gly Leu Pro Gly Asp Thr Gly
    530                 535                 540
```

-continued

```
Pro Lys Gly Asp Arg Gly Phe Asp Gly Leu Pro Gly Leu Pro Gly Glu
545                 550                 555                 560

Lys Gly Gln Arg Gly Asp Phe Gly Arg Val Gly Gln Pro Gly Pro Pro
                565                 570                 575

Gly Glu Asp Gly Val Lys Gly Leu Gln Gly Pro Pro Gly Pro Thr Gly
            580                 585                 590

Gln Ala Gly Glu Pro Gly Pro Arg Gly Leu Ile Gly Pro Arg Gly Leu
        595                 600                 605

Pro Gly Pro Leu Gly Arg Pro Gly Val Thr Gly Ser Asp Gly Ala Pro
    610                 615                 620

Gly Ala Lys Gly Asn Val Gly Pro Pro Gly Glu Pro Gly Pro Pro Gly
625                 630                 635                 640

Gln Gln Gly Asn His Gly Ser Gln Gly Ile Pro Gly Pro Gln Gly Pro
                645                 650                 655

Ile Gly Thr Pro Gly Glu Lys Gly Pro Pro Gly Asn Pro Gly Ile Pro
            660                 665                 670

Gly Val Pro Gly Ser Glu Gly Pro Pro Gly His Pro Gly His Glu Gly
        675                 680                 685

Pro Thr Gly Glu Lys Gly Ala Gln Gly Pro Pro Gly Ser Ala Gly Pro
    690                 695                 700

Arg Gly Tyr Pro Gly Leu Arg Gly Val Lys Gly Thr Ser Gly Asn Arg
705                 710                 715                 720

Gly Leu Gln Gly Glu Lys Gly Glu Arg Gly Glu Asp Gly Phe Pro Gly
                725                 730                 735

Phe Lys Gly Asp Glu Gly Pro Lys Gly Asp Arg Gly Asn Pro Gly Pro
            740                 745                 750

Pro Gly Pro Arg Gly Glu Asp Gly Pro Glu Gly Gln Lys Gly Pro Gly
        755                 760                 765

Gly Leu Pro Gly Asp Glu Gly Pro Pro Gly Ala Ala Gly Glu Lys Gly
    770                 775                 780

Lys Leu Gly Val Pro Gly Leu Pro Gly Tyr Pro Gly Arg Pro Gly Pro
785                 790                 795                 800

Lys Gly Ser Ile Gly Phe Pro Gly Pro Leu Gly Pro Leu Gly Glu Lys
                805                 810                 815

Gly Lys Arg Gly Lys Ala Gly Gln Pro Gly Glu Glu Gly Glu Arg Gly
            820                 825                 830

Thr Pro Gly Thr Arg Gly Asp Arg Gly Gln Pro Gly Ala Thr Gly Gln
        835                 840                 845

Pro Gly Pro Lys Gly Asp Val Gly Gln Asn Gly Ser Pro Gly Pro Pro
    850                 855                 860

Gly Glu Lys Gly Leu Pro Gly Leu Gln Gly Pro Pro Gly Phe Pro Gly
865                 870                 875                 880

Pro Lys Gly Pro Pro Gly Pro Gln Gly Lys Asp Gly Ile Ser Gly His
                885                 890                 895

Pro Gly Gln Arg Gly Glu Leu Gly Phe Gln Gly Leu Thr Gly Pro Pro
            900                 905                 910

Gly Pro Ala Gly Val Leu Gly Pro Gln Gly Lys Val Gly Asp Val Gly
        915                 920                 925

Pro Leu Gly Glu Arg Gly Pro Pro Gly Pro Pro Gly Pro Pro Gly Glu
    930                 935                 940

Gln Gly Leu Pro Gly Ile Glu Gly Arg Glu Gly Ala Lys Gly Glu Leu
945                 950                 955                 960

Gly Pro Leu Gly Ser Val Gly Lys Glu Gly Pro Pro Gly Pro Arg Gly
```

-continued

```
                965                 970                 975

Phe Pro Gly Pro Gln Gly Ala Pro Gly Asp Pro Gly Pro Ile Gly Leu
            980                 985                 990

Lys Gly Asp Lys Gly Pro Pro Gly Pro Val Gly Ala Asn Gly Ser Pro
        995                1000                1005

Gly Glu Arg Gly Pro Val Gly Pro Ser Gly Gly Ile Gly Leu Pro Gly
   1010                1015                1020

Gln Ser Gly Gly Gln Gly Pro Ile Gly Pro Ala Gly Glu Lys Gly Ser
1025                1030                1035                1040

Pro Gly Glu Arg Gly Thr Pro Gly Pro Thr Gly Lys Asp Gly Ile Pro
               1045                1050                1055

Gly Pro Pro Gly Leu Gln Gly Pro Ser Gly Ala Ala Gly Pro Ser Gly
           1060                1065                1070

Glu Glu Gly Asp Lys Gly Glu Val Gly Met Pro Gly His Lys Gly Ser
       1075                1080                1085

Lys Gly Asp Lys Gly Asp Ala Gly Pro Pro Gly Pro Thr Gly Ile Arg
   1090                1095                1100

Gly Pro Ala Gly His Ser Gly Leu Pro Gly Ala Asp Gly Ala Gln Gly
1105                1110                1115                1120

Arg Arg Gly Pro Pro Gly Leu Phe Gly Gln Lys Gly Asp Asp Gly Val
               1125                1130                1135

Arg Gly Phe Val Gly Val Ile Gly Pro Pro Gly Leu Gln Gly Leu Pro
           1140                1145                1150

Gly Pro Pro Gly Glu Lys Gly Glu Val Gly Asp Val Gly Ser Met Gly
       1155                1160                1165

Pro His Gly Ala Pro Gly Pro Arg Gly Pro Pro Gly Pro Ser Gly Ser
   1170                1175                1180

Glu Gly Pro Pro Gly Leu Pro Gly Gly Val Gly Gln Pro Gly Ala Val
1185                1190                1195                1200

Gly Glu Lys Gly Glu Pro Gly Asp Ala Gly Asp Ala Gly Pro Pro Gly
               1205                1210                1215

Ile Pro Gly Ile Pro Gly Pro Lys Gly Glu Ile Gly Glu Lys Gly Asp
           1220                1225                1230

Ser Gly Pro Ser Gly Ala Ala Gly Pro Pro Gly Lys Lys Gly Pro Pro
       1235                1240                1245

Gly Glu Asp Gly Ser Lys Gly Asn Met Gly Pro Thr Gly Leu Pro Gly
   1250                1255                1260

Asp Leu Gly Pro Pro Gly Asp Pro Gly Val Pro Gly Ile Asp Gly Ile
1265                1270                1275                1280

Pro Gly Glu Lys Gly Asn Ala Gly Asp Ile Gly Gly Pro Gly Pro Pro
               1285                1290                1295

Gly Ala Ser Gly Glu Pro Gly Ala Arg Gly Leu Pro Gly Lys Arg Gly
           1300                1305                1310

Ser Pro Gly Arg Met Gly Pro Glu Gly Arg Glu Gly Glu Lys Gly Ala
       1315                1320                1325

Lys Gly Asp Ala Gly Pro Asp Gly Pro Pro Gly Arg Thr Gly Pro Ile
   1330                1335                1340

Gly Ala Arg Gly Pro Pro Gly Arg Ile Gly Pro Asp Gly Leu Pro Gly
1345                1350                1355                1360

Ile Pro Gly Pro Val Gly Glu Pro Gly Leu Leu Gly Pro Pro Gly Leu
               1365                1370                1375

Ile Gly Pro Pro Gly Pro Leu Gly Pro Pro Gly Leu Pro Gly Leu Lys
           1380                1385                1390
```

-continued

```
Gly Asp Ala Gly Pro Lys Gly Glu Lys Gly His Ile Gly Leu Ile Gly
       1395                1400                1405

Leu Ile Gly Pro Pro Gly Glu Ala Gly Glu Lys Gly Asp Gln Gly Leu
   1410                1415                1420

Pro Gly Val Gln Gly Pro Pro Gly Leu Gln Gly Asp Pro Gly Leu Pro
1425                1430                1435                1440

Gly Pro Val Gly Ser Leu Gly His Pro Gly Pro Pro Gly Val Val Gly
               1445                1450                1455

Pro Leu Gly Gln Lys Gly Ser Lys Gly Ser Pro Gly Ser Leu Gly Pro
           1460                1465                1470

Arg Gly Asp Pro Gly Pro Ala Gly Pro Pro Gly Pro Pro Gly Ser Pro
       1475                1480                1485

Ala Glu Val His Gly Leu Arg Arg Arg Arg Ser Val Thr Asp Thr Leu
   1490                1495                1500

Glu Gly Gly Leu Glu Glu Val Met Ala Ser Leu Asn Ser Leu Ser Leu
1505                1510                1515                1520

Glu Leu Gln Gln Leu Gln Arg Pro Leu Gly Thr Ala Glu Ser Pro Gly
               1525                1530                1535

Leu Met Cys Arg Glu Leu His Arg Asp His Pro His Leu Pro Asp Gly
           1540                1545                1550

Glu Tyr Trp Ile Asp Pro Asn Gln Gly Cys Ala Arg Asp Ala Phe Lys
       1555                1560                1565

Val Phe Cys Asn Phe Thr Ala Gly Gly Glu Thr Cys Leu Tyr Pro Asp
   1570                1575                1580

Lys Lys Phe Glu Thr Val Lys Leu Ala Ser Trp Ser Arg Glu Lys Pro
1585                1590                1595                1600

Gly Gly Trp Tyr Ser Thr Phe Arg Arg Gly Lys Lys Phe Ser Tyr Val
               1605                1610                1615

Asp Ala Asp Gly Ser Pro Val Asn Val Val Gln Leu Thr Phe Leu Lys
           1620                1625                1630

Leu Leu Ser Ala Ala Ala His Gln Arg Phe Thr Tyr Ile Cys Gln Asn
       1635                1640                1645

Ser Val Ala Trp Leu Asp Glu Ala Ala Gly Asp His Arg His Ser Ile
   1650                1655                1660

Arg Phe Gln Gly Thr Asn Trp Glu Glu Leu Ser Phe Asn Gln Thr Thr
1665                1670                1675                1680

Ala Ala Thr Ile Lys Val Ser His Asp Gly Cys Arg Val Arg Lys Gly
               1685                1690                1695

Gln Ala Lys Thr Leu Phe Glu Phe Ser Ser Ser Val Gly Phe Leu Pro
           1700                1705                1710

Leu Trp Asp Val Ala Ala Ser Asp Phe Gly Gln Thr Asn Gln Lys Phe
       1715                1720                1725

Gly Phe Glu Leu Gly Ser Ile Cys Phe Ser Ser
   1730                1735
```

<210> SEQ ID NO 3
<211> LENGTH: 6200
<212> TYPE: DNA
<213> ORGANISM: Homo sapiens
<220> FEATURE:
<221> NAME/KEY: CDS
<222> LOCATION: (87)..(5321)

<400> SEQUENCE: 3

```
gcgagtgact gcaccgagcc cgagaagtcg ccgcgccccg cagccgcccc gactggttcc     60
```

-continued

```
ccgccttgcc cgtgggcccc gccggg atg ggg aac cgc cgg gac ctg ggc cag      113
                             Met Gly Asn Arg Arg Asp Leu Gly Gln
                               1               5

ccg cgg gcc ggt ctc tgc ctg ctc ctg gcc gcg ctg cag ctt ctg ccg      161
Pro Arg Ala Gly Leu Cys Leu Leu Leu Ala Ala Leu Gln Leu Leu Pro
 10                  15                  20                  25

ggg acg cag gcc gat cct gtg gat gtc ctg aag gcc ctg ggt gtg cag      209
Gly Thr Gln Ala Asp Pro Val Asp Val Leu Lys Ala Leu Gly Val Gln
                 30                  35                  40

gga ggc cag gct ggg gtc ccc gag ggg cct ggc ttc tgt ccc cag agg      257
Gly Gly Gln Ala Gly Val Pro Glu Gly Pro Gly Phe Cys Pro Gln Arg
             45                  50                  55

act cca gag ggt gac cgg gca ttc aga att ggc cag gcc agc acg ctc      305
Thr Pro Glu Gly Asp Arg Ala Phe Arg Ile Gly Gln Ala Ser Thr Leu
         60                  65                  70

ggc atc ccc acg tgg gaa ctc ttt cca gaa ggc cac ttt cct gag aac      353
Gly Ile Pro Thr Trp Glu Leu Phe Pro Glu Gly His Phe Pro Glu Asn
     75                  80                  85

ttc tcc ttg ctg atc acc ttg cgg gga cag cca gcc aat cag tct gtc      401
Phe Ser Leu Leu Ile Thr Leu Arg Gly Gln Pro Ala Asn Gln Ser Val
 90                  95                 100                 105

ctg ctg tcc att tat gat gaa agg ggt gcc cgg cag ttg ggc ctg gca      449
Leu Leu Ser Ile Tyr Asp Glu Arg Gly Ala Arg Gln Leu Gly Leu Ala
                110                 115                 120

ctg ggg cca gcg ctg ggt ctc cta ggt gac ccc ttc cgc ccc ctc ccc      497
Leu Gly Pro Ala Leu Gly Leu Leu Gly Asp Pro Phe Arg Pro Leu Pro
            125                 130                 135

cag cag gtc aac ctc aca gat ggc agg tgg cac cgt gtg gcc gtc agc      545
Gln Gln Val Asn Leu Thr Asp Gly Arg Trp His Arg Val Ala Val Ser
        140                 145                 150

ata gat ggt gag atg gtg acc ctg gta gct gac tgt gaa gct cag ccc      593
Ile Asp Gly Glu Met Val Thr Leu Val Ala Asp Cys Glu Ala Gln Pro
    155                 160                 165

cct gtt ttg ggc cat ggc ccc cgc ttc atc agc ata gct gga ctc act      641
Pro Val Leu Gly His Gly Pro Arg Phe Ile Ser Ile Ala Gly Leu Thr
170                 175                 180                 185

gtg ctg ggg acc cag gac ctt ggg gaa aag act ttc gag gga gac att      689
Val Leu Gly Thr Gln Asp Leu Gly Glu Lys Thr Phe Glu Gly Asp Ile
                190                 195                 200

cag gag ctg ctg ata agc cca gat cct cag gct gcc ttc cag gct tgt      737
Gln Glu Leu Leu Ile Ser Pro Asp Pro Gln Ala Ala Phe Gln Ala Cys
            205                 210                 215

gag cgg tac ctc ccc gac tgt gac aac ctg gca ccg gca gcc aca gtg      785
Glu Arg Tyr Leu Pro Asp Cys Asp Asn Leu Ala Pro Ala Ala Thr Val
        220                 225                 230

gct ccc cag ggt gaa cca gaa acc cct cgt cct cgg cgg aag ggg aag      833
Ala Pro Gln Gly Glu Pro Glu Thr Pro Arg Pro Arg Arg Lys Gly Lys
    235                 240                 245

gga aaa ggg agg aag aaa ggg cga ggt cgc aag ggg aag ggc agg aaa      881
Gly Lys Gly Arg Lys Lys Gly Arg Gly Arg Lys Gly Lys Gly Arg Lys
250                 255                 260                 265

aag aac aag gaa att tgg acc tca agt cca cct cct gac tcc gca gag      929
Lys Asn Lys Glu Ile Trp Thr Ser Ser Pro Pro Pro Asp Ser Ala Glu
                270                 275                 280

aac cag acc tcc act gac atc ccc aag aca gag act cca gct cca aat      977
Asn Gln Thr Ser Thr Asp Ile Pro Lys Thr Glu Thr Pro Ala Pro Asn
            285                 290                 295

ctg cct ccg acc ccc acg cct ttg gtc gtc acc tcc act gtg act act     1025
Leu Pro Pro Thr Pro Thr Pro Leu Val Val Thr Ser Thr Val Thr Thr
```

-continued

```
        300                 305                 310

gga ctc aat gcc acg atc cta gag ggg agc ttg gac cct gac agt gga     1073
Gly Leu Asn Ala Thr Ile Leu Glu Gly Ser Leu Asp Pro Asp Ser Gly
    315                 320                 325

acc gag ctg ggg acc ctg gag acc aag gca gcc agg gag gat gaa gaa     1121
Thr Glu Leu Gly Thr Leu Glu Thr Lys Ala Ala Arg Glu Asp Glu Glu
330                 335                 340                 345

gga gat gat tcc acc atg ggc cct gac ttc cgg gca gca gaa tat cca     1169
Gly Asp Asp Ser Thr Met Gly Pro Asp Phe Arg Ala Ala Glu Tyr Pro
                350                 355                 360

tct cgg act cag ttc cag atc ttt cct ggt gct gga gag aaa gga gca     1217
Ser Arg Thr Gln Phe Gln Ile Phe Pro Gly Ala Gly Glu Lys Gly Ala
            365                 370                 375

aaa gga gag ccc gca gtg att gaa aag ggg cag cag ttt gag gga cct     1265
Lys Gly Glu Pro Ala Val Ile Glu Lys Gly Gln Gln Phe Glu Gly Pro
        380                 385                 390

cca gga gcc cca gga ccc caa ggg gtg gtt ggc ccc tca ggc cct ccc     1313
Pro Gly Ala Pro Gly Pro Gln Gly Val Val Gly Pro Ser Gly Pro Pro
    395                 400                 405

ggc ccc cca gga ttc cct ggc gac cct ggt cca ccg ggc cct gct ggc     1361
Gly Pro Pro Gly Phe Pro Gly Asp Pro Gly Pro Pro Gly Pro Ala Gly
410                 415                 420                 425

ctc cca gga atc ccc ggc att gat ggg atc cga ggc cca ccg ggc act     1409
Leu Pro Gly Ile Pro Gly Ile Asp Gly Ile Arg Gly Pro Pro Gly Thr
                430                 435                 440

gtg atc atg atg ccg ttc cag ttt gca ggc ggc tcc ttt aaa ggc ccc     1457
Val Ile Met Met Pro Phe Gln Phe Ala Gly Gly Ser Phe Lys Gly Pro
            445                 450                 455

cca gtc tca ttc cag cag gcc cag gct cag gca gtt ctg cag cag act     1505
Pro Val Ser Phe Gln Gln Ala Gln Ala Gln Ala Val Leu Gln Gln Thr
        460                 465                 470

cag ctc tct atg aaa ggc ccc cct ggt cca gtg ggg ctc act ggg cgc     1553
Gln Leu Ser Met Lys Gly Pro Pro Gly Pro Val Gly Leu Thr Gly Arg
    475                 480                 485

cca ggc cct gtg ggt ctc ccc ggg cat cca ggt ctg aaa gga gag gag     1601
Pro Gly Pro Val Gly Leu Pro Gly His Pro Gly Leu Lys Gly Glu Glu
490                 495                 500                 505

gga gca gaa ggg cca cag ggt ccc cga ggc ctg cag gga cct cat gga     1649
Gly Ala Glu Gly Pro Gln Gly Pro Arg Gly Leu Gln Gly Pro His Gly
                510                 515                 520

ccc cct ggc cga gtg ggc aag atg ggc cgc cct gga gca gat gga gct     1697
Pro Pro Gly Arg Val Gly Lys Met Gly Arg Pro Gly Ala Asp Gly Ala
            525                 530                 535

cgg ggc ctc cca ggg gac act gga cct aag ggt gat cgt ggc ttc gat     1745
Arg Gly Leu Pro Gly Asp Thr Gly Pro Lys Gly Asp Arg Gly Phe Asp
        540                 545                 550

ggc ctc cct ggg ctg cct ggt gag aag ggc caa agg ggt gac ttt ggc     1793
Gly Leu Pro Gly Leu Pro Gly Glu Lys Gly Gln Arg Gly Asp Phe Gly
    555                 560                 565

cat gtg ggg caa ccc ggt ccc cca gga gag gat ggt gag agg gga gca     1841
His Val Gly Gln Pro Gly Pro Pro Gly Glu Asp Gly Glu Arg Gly Ala
570                 575                 580                 585

gag gga cct cca ggg ccc act ggc cag gct ggg gag ccg ggt cca cga     1889
Glu Gly Pro Pro Gly Pro Thr Gly Gln Ala Gly Glu Pro Gly Pro Arg
                590                 595                 600

gga ctg ctt ggc ccc aga ggc tct cct ggc ccc acg ggt cgc ccg ggt     1937
Gly Leu Leu Gly Pro Arg Gly Ser Pro Gly Pro Thr Gly Arg Pro Gly
            605                 610                 615

gtg act gga att gat ggt gct cct ggt gcc aaa ggc aat gtg ggt cct     1985
```

-continued

```
Val Thr Gly Ile Asp Gly Ala Pro Gly Ala Lys Gly Asn Val Gly Pro
        620                 625                 630

cca gga gaa cca ggc cct ccg gga cag cag gga aac cat ggg tcc cag      2033
Pro Gly Glu Pro Gly Pro Pro Gly Gln Gln Gly Asn His Gly Ser Gln
    635                 640                 645

gga ctc ccc ggt ccc cag gga ctc att ggc act cct ggg gag aag ggt      2081
Gly Leu Pro Gly Pro Gln Gly Leu Ile Gly Thr Pro Gly Glu Lys Gly
650                 655                 660                 665

ccc cct gga aac cca gga att cca ggc ctc cca gga tcc gat ggc cct      2129
Pro Pro Gly Asn Pro Gly Ile Pro Gly Leu Pro Gly Ser Asp Gly Pro
                670                 675                 680

ctg ggt cac cca gga cat gag ggc ccc acg gga gag aaa ggg gct cag      2177
Leu Gly His Pro Gly His Glu Gly Pro Thr Gly Glu Lys Gly Ala Gln
            685                 690                 695

ggt cca cca ggg tcg gca ggc cct ccg ggc tat cct gga cct cgg gga      2225
Gly Pro Pro Gly Ser Ala Gly Pro Pro Gly Tyr Pro Gly Pro Arg Gly
        700                 705                 710

gtg aag ggc act tca ggc aac cgg ggc ctc cag ggg gag aaa ggc gag      2273
Val Lys Gly Thr Ser Gly Asn Arg Gly Leu Gln Gly Glu Lys Gly Glu
    715                 720                 725

aag gga gag gac ggc ttc cca ggc ttc aag ggc gat gtg ggg ctc aaa      2321
Lys Gly Glu Asp Gly Phe Pro Gly Phe Lys Gly Asp Val Gly Leu Lys
730                 735                 740                 745

ggt gat cag ggg aaa ccc gga gct cca ggt ccc cgg gga gag gat ggt      2369
Gly Asp Gln Gly Lys Pro Gly Ala Pro Gly Pro Arg Gly Glu Asp Gly
                750                 755                 760

cct gag ggg ccg aag ggg cag gcg ggg cag gct ggc gag gag ggg ccc      2417
Pro Glu Gly Pro Lys Gly Gln Ala Gly Gln Ala Gly Glu Glu Gly Pro
            765                 770                 775

cca ggc tca gct ggg gag aag ggc aag ctt ggg gtg cca ggc ctc cca      2465
Pro Gly Ser Ala Gly Glu Lys Gly Lys Leu Gly Val Pro Gly Leu Pro
        780                 785                 790

ggt tat cca gga cgc cct gga cct aag gga tct att gga ttt ccc ggt      2513
Gly Tyr Pro Gly Arg Pro Gly Pro Lys Gly Ser Ile Gly Phe Pro Gly
    795                 800                 805

ccc ctg gga ccc ata gga gag aaa ggg aag tcg gga aag aca ggg cag      2561
Pro Leu Gly Pro Ile Gly Glu Lys Gly Lys Ser Gly Lys Thr Gly Gln
810                 815                 820                 825

cca ggc ctg gaa gga gag cgg gga cca cca ggt tcc cgt gga gag agg      2609
Pro Gly Leu Glu Gly Glu Arg Gly Pro Pro Gly Ser Arg Gly Glu Arg
                830                 835                 840

ggg caa ccg ggt gcc aca ggg caa cca ggc ccc aag ggc gat gtg ggc      2657
Gly Gln Pro Gly Ala Thr Gly Gln Pro Gly Pro Lys Gly Asp Val Gly
            845                 850                 855

cag gat gga gcc cct ggg atc cct gga gaa aag ggc ctc cct ggt ctg      2705
Gln Asp Gly Ala Pro Gly Ile Pro Gly Glu Lys Gly Leu Pro Gly Leu
        860                 865                 870

caa ggc cct cca gga ttc cct ggg cca aag ggc ccc cct ggt cac caa      2753
Gln Gly Pro Pro Gly Phe Pro Gly Pro Lys Gly Pro Pro Gly His Gln
    875                 880                 885

ggt aaa gat ggg cga cca ggg cac cct gga cag aga gga gaa ctg ggc      2801
Gly Lys Asp Gly Arg Pro Gly His Pro Gly Gln Arg Gly Glu Leu Gly
890                 895                 900                 905

ttc caa ggt cag aca ggc ccg cct gga cca gct ggt gtc tta ggc cct      2849
Phe Gln Gly Gln Thr Gly Pro Pro Gly Pro Ala Gly Val Leu Gly Pro
                910                 915                 920

cag gga aag aca gga gaa gtg gga cct cta ggt gaa agg ggg cct cca      2897
Gln Gly Lys Thr Gly Glu Val Gly Pro Leu Gly Glu Arg Gly Pro Pro
            925                 930                 935
```

-continued

```
ggc ccc cct gga cct cct ggt gaa caa ggt ctt cct ggc ctg gaa ggc     2945
Gly Pro Pro Gly Pro Pro Gly Glu Gln Gly Leu Pro Gly Leu Glu Gly
        940                 945                 950

aga gag ggg gcc aag ggg gaa ctg gga cca cca gga ccc ctt ggg aaa     2993
Arg Glu Gly Ala Lys Gly Glu Leu Gly Pro Pro Gly Pro Leu Gly Lys
    955                 960                 965

gaa ggg cca gct gga ctc agg ggc ttt ccc ggc ccc aaa ggg ggc cct     3041
Glu Gly Pro Ala Gly Leu Arg Gly Phe Pro Gly Pro Lys Gly Gly Pro
970                 975                 980                 985

ggg gac ccg gga cct act ggc tta aag ggt gat aag ggc ccc cca ggg     3089
Gly Asp Pro Gly Pro Thr Gly Leu Lys Gly Asp Lys Gly Pro Pro Gly
                990                 995                1000

cct gtg ggg gcc aat ggc tcc cct ggt gag cgc ggt cct ttg ggc cca     3137
Pro Val Gly Ala Asn Gly Ser Pro Gly Glu Arg Gly Pro Leu Gly Pro
           1005                1010                1015

gca gga ggc att gga ctt cct ggc caa agt ggc agc gaa ggc ccc gtt     3185
Ala Gly Gly Ile Gly Leu Pro Gly Gln Ser Gly Ser Glu Gly Pro Val
       1020                1025                1030

ggc cct gca ggc aag aag ggg tcc cgg gga gaa cgt ggc ccc cct ggc     3233
Gly Pro Ala Gly Lys Lys Gly Ser Arg Gly Glu Arg Gly Pro Pro Gly
   1035                1040                1045

ccc act ggc aaa gat ggg atc cca ggg ccc ctg ggg cct ctg gga ccc     3281
Pro Thr Gly Lys Asp Gly Ile Pro Gly Pro Leu Gly Pro Leu Gly Pro
1050                1055                1060                1065

cct gga gct gct ggg cct tct ggc gag gaa ggg gac aag ggg gat gtg     3329
Pro Gly Ala Ala Gly Pro Ser Gly Glu Glu Gly Asp Lys Gly Asp Val
               1070                1075                1080

ggt gcc ccc gga cac aag ggg agt aaa ggc gat aaa gga gac gcg ggc     3377
Gly Ala Pro Gly His Lys Gly Ser Lys Gly Asp Lys Gly Asp Ala Gly
           1085                1090                1095

cca cct gga caa cca ggg ata cgg ggt cct gca gga cac cca ggt ccc     3425
Pro Pro Gly Gln Pro Gly Ile Arg Gly Pro Ala Gly His Pro Gly Pro
       1100                1105                1110

ccg gga gca gac ggg gct cag ggg cgc cgg gga ccc cca ggc ctc ttt     3473
Pro Gly Ala Asp Gly Ala Gln Gly Arg Arg Gly Pro Pro Gly Leu Phe
   1115                1120                1125

ggg cag aaa gga gat gac gga gtc aga ggc ttt gtg ggg gtg att ggc     3521
Gly Gln Lys Gly Asp Asp Gly Val Arg Gly Phe Val Gly Val Ile Gly
1130                1135                1140                1145

cct cct gga ctg cag ggg ctg cca ggc cct ccg gga gag aaa ggg gag     3569
Pro Pro Gly Leu Gln Gly Leu Pro Gly Pro Pro Gly Glu Lys Gly Glu
               1150                1155                1160

gtc gga gac gtc ggg tcc atg ggt ccc cat gga gct cca ggt cct cgg     3617
Val Gly Asp Val Gly Ser Met Gly Pro His Gly Ala Pro Gly Pro Arg
           1165                1170                1175

ggt ccc caa ggc ccc act gga tca gag ggc act cca ggg ctg cct gga     3665
Gly Pro Gln Gly Pro Thr Gly Ser Glu Gly Thr Pro Gly Leu Pro Gly
       1180                1185                1190

gga gtt ggt cag cca ggc gcc gtg ggt gag aag ggt gag cga ggg gac     3713
Gly Val Gly Gln Pro Gly Ala Val Gly Glu Lys Gly Glu Arg Gly Asp
   1195                1200                1205

gct gga gac cca ggg cct cca gga gcc cca ggc atc ccg ggg ccc aag     3761
Ala Gly Asp Pro Gly Pro Pro Gly Ala Pro Gly Ile Pro Gly Pro Lys
1210                1215                1220                1225

gga gac att ggt gaa aag ggg gac tca ggc cca tct gga gct gct gga     3809
Gly Asp Ile Gly Glu Lys Gly Asp Ser Gly Pro Ser Gly Ala Ala Gly
               1230                1235                1240

ccc cca ggc aag aaa ggt ccc cct gga gag gat gga gcc aaa ggg agc     3857
Pro Pro Gly Lys Lys Gly Pro Pro Gly Glu Asp Gly Ala Lys Gly Ser
           1245                1250                1255
```

-continued

```
gtg ggc ccc acg ggg ctg ccc gga gat cta ggg ccc cca gga gac cct     3905
Val Gly Pro Thr Gly Leu Pro Gly Asp Leu Gly Pro Pro Gly Asp Pro
       1260                1265                1270

gga gtt tca ggc ata gat ggt tcc cca ggg gag aag gga gac cct ggt     3953
Gly Val Ser Gly Ile Asp Gly Ser Pro Gly Glu Lys Gly Asp Pro Gly
   1275                1280                1285

gat gtt ggg gga ccg ggt ccg cct gga gct tct ggg gag ccc ggc gcc     4001
Asp Val Gly Gly Pro Gly Pro Pro Gly Ala Ser Gly Glu Pro Gly Ala
1290                1295                1300                1305

ccc ggg ccc ccc ggc aag agg ggt cct tca ggc cac atg ggt cga gaa     4049
Pro Gly Pro Pro Gly Lys Arg Gly Pro Ser Gly His Met Gly Arg Glu
               1310                1315                1320

ggc aga gaa ggg gag aaa ggt gcc aag ggg gag cca ggt cct gat ggg     4097
Gly Arg Glu Gly Glu Lys Gly Ala Lys Gly Glu Pro Gly Pro Asp Gly
           1325                1330                1335

ccc cca ggg agg acg ggt cca atg ggg gct aga ggg ccc cct gga cgt     4145
Pro Pro Gly Arg Thr Gly Pro Met Gly Ala Arg Gly Pro Pro Gly Arg
       1340                1345                1350

gtg ggg cct gag ggt ctt cga ggg atc cct ggc cct gtg ggt gaa cca     4193
Val Gly Pro Glu Gly Leu Arg Gly Ile Pro Gly Pro Val Gly Glu Pro
   1355                1360                1365

ggc ctc ctg gga gcc cct gga cag atg ggc cct cct ggc ccc ctg ggg     4241
Gly Leu Leu Gly Ala Pro Gly Gln Met Gly Pro Pro Gly Pro Leu Gly
1370                1375                1380                1385

ccc tct ggc ctc cca ggg ctg aag gga gac act ggc ccc aag ggg gaa     4289
Pro Ser Gly Leu Pro Gly Leu Lys Gly Asp Thr Gly Pro Lys Gly Glu
               1390                1395                1400

aag ggc cac att gga ttg atc ggt ctc att ggc ccc ccg gga gaa gct     4337
Lys Gly His Ile Gly Leu Ile Gly Leu Ile Gly Pro Pro Gly Glu Ala
           1405                1410                1415

ggt gag aaa gga gat cag ggg ttg cca ggc gtg cag gga ccc cct ggt     4385
Gly Glu Lys Gly Asp Gln Gly Leu Pro Gly Val Gln Gly Pro Pro Gly
       1420                1425                1430

ccc aag gga gac cct ggt ccc cct ggt ccc att ggc tct ctg ggc cac     4433
Pro Lys Gly Asp Pro Gly Pro Pro Gly Pro Ile Gly Ser Leu Gly His
   1435                1440                1445

cct ggg ccc cca ggt gtg gcg ggc cct cta gga cag aaa ggc tca aaa     4481
Pro Gly Pro Pro Gly Val Ala Gly Pro Leu Gly Gln Lys Gly Ser Lys
1450                1455                1460                1465

ggg tct ccg ggg tcc atg ggc ccc cgt gga gac act gga cct gca ggc     4529
Gly Ser Pro Gly Ser Met Gly Pro Arg Gly Asp Thr Gly Pro Ala Gly
               1470                1475                1480

cca cca ggc ccc ccg ggt gcc cct gcc gag ctg cat ggg ctg cgc agg     4577
Pro Pro Gly Pro Pro Gly Ala Pro Ala Glu Leu His Gly Leu Arg Arg
           1485                1490                1495

cgc cgg cgc ttc gtc cca gtc ccg ctt cca gtc gtg gag ggc ggc ctg     4625
Arg Arg Arg Phe Val Pro Val Pro Leu Pro Val Val Glu Gly Gly Leu
       1500                1505                1510

gag gag gtg ctg gcc tcg ctc aca tcg ctg agc ttg gag ctg gag cag     4673
Glu Glu Val Leu Ala Ser Leu Thr Ser Leu Ser Leu Glu Leu Glu Gln
   1515                1520                1525

ctg cgg cgt cct ccc ggc act gcg gag cgc ccg ggc ctc gtg tgc cac     4721
Leu Arg Arg Pro Pro Gly Thr Ala Glu Arg Pro Gly Leu Val Cys His
1530                1535                1540                1545

gag ctg cac cgc aac cac ccg cac ctg cct gat ggg gaa tac tgg att     4769
Glu Leu His Arg Asn His Pro His Leu Pro Asp Gly Glu Tyr Trp Ile
               1550                1555                1560

gac ccc aac cag ggc tgc gcg cgg gac tcg ttc agg gtt ttt tgc aac     4817
Asp Pro Asn Gln Gly Cys Ala Arg Asp Ser Phe Arg Val Phe Cys Asn
```

-continued

```
          1565                1570                1575

ttc acg gcg gga gga gag acc tgc ctc tat ccc gac aag aag ttt gag     4865
Phe Thr Ala Gly Gly Glu Thr Cys Leu Tyr Pro Asp Lys Lys Phe Glu
      1580                1585                1590

atc gtg aaa ttg gcc tcc tgg tcc aag gaa aag cct gga ggc tgg tat     4913
Ile Val Lys Leu Ala Ser Trp Ser Lys Glu Lys Pro Gly Gly Trp Tyr
   1595                1600                1605

agc aca ttc cgt cga ggg aag aag ttc tcc tac gtg gac gcc gac ggg     4961
Ser Thr Phe Arg Arg Gly Lys Lys Phe Ser Tyr Val Asp Ala Asp Gly
1610                1615                1620                1625

tcc cca gtg aat gtc gtg cag ctg aac ttc ctg aaa ctg ctg agt gcc     5009
Ser Pro Val Asn Val Val Gln Leu Asn Phe Leu Lys Leu Leu Ser Ala
               1630                1635                1640

aca gct cgc cag aac ttc acc tac tcc tgc cag aat gca gct gcc tgg     5057
Thr Ala Arg Gln Asn Phe Thr Tyr Ser Cys Gln Asn Ala Ala Ala Trp
          1645                1650                1655

ctg gac gaa gcc acg ggt gac tac agc cac tcc gcc cgc ttc ctt ggc     5105
Leu Asp Glu Ala Thr Gly Asp Tyr Ser His Ser Ala Arg Phe Leu Gly
      1660                1665                1670

acc aat gga gag gag ctg tct ttc aac cag acg aca gca acc act gtc     5153
Thr Asn Gly Glu Glu Leu Ser Phe Asn Gln Thr Thr Ala Thr Thr Val
   1675                1680                1685

agc gtc ccc cag gat ggc tgc cgg ctc cgg aaa gga cag acg aag acc     5201
Ser Val Pro Gln Asp Gly Cys Arg Leu Arg Lys Gly Gln Thr Lys Thr
1690                1695                1700                1705

ctt ttc gaa ttc agc tct tct cga gcg gga ttt ctg ccc ctg tgg gat     5249
Leu Phe Glu Phe Ser Ser Ser Arg Ala Gly Phe Leu Pro Leu Trp Asp
               1710                1715                1720

gtg gcg gcc act gac ttt ggc cag acg aac caa aag ttt ggg ttt gaa     5297
Val Ala Ala Thr Asp Phe Gly Gln Thr Asn Gln Lys Phe Gly Phe Glu
          1725                1730                1735

ctg ggc ccc gtc tgc ttc agc agc tgagagtgtc cggggtggga gggaccgtga    5351
Leu Gly Pro Val Cys Phe Ser Ser
      1740                1745

gggagcccca gaatggggtg catttggtgc tgaggctttg aagccaccgt atttttcgtt   5411

acctgtgact atggagccaa tgggatgtga cttcgctcat cacggtcagt cattccttct   5471

cctttccagg gtgctggggg ctggggttcc ctggcccaag ggtccagcct cctctcaccc   5531

cattccaggt ggcatactgc agtctggctc tttctcccct ccctccccac ccaagcctca   5591

cctccccacc ccttgaaccc ccatgcaatg agcttctaac tcagagctga tgaacaaaag   5651

cccccccacc cccaatgcct gcctcctcac tcctccgtcg ctgcccttca caccttttgg   5711

tgctacccct ccccagagtt aagcactgga tgtctcctga tcccaggctg ggacccctac   5771

ccccaccccc tttgatcctt tctacttcca cggtgaaagg actgaggtcg gactacagag   5831

ggaagaggga cttcccttga ctgggttgtg tttcttttcc tgcctcagcc cagctctgca   5891

aatcccctcc ccctgcccct cacctcccca ggctcacctt gccatgccag gtggtttggg   5951

gaccaagatg ttggggggt gaatcaggat cctaatggtg ctgccctatt tatacctggg    6011

tctgtattaa aagggaaagt ccccccctgtt gtagatttca tctgcttcct ccttagggaa  6071

ggctgggata tgatgagaga ttccagccca agcccggccc cccaccgcca ggccataggg   6131

cataatttgc atctcaaatc tgagaataaa ctgatgaact gtggaaaaaa aaaaaaaaaa   6191

aaaaaaaaa                                                           6200

<210> SEQ ID NO 4
<211> LENGTH: 1745
```

-continued

<212> TYPE: PRT
<213> ORGANISM: Homo sapiens

<400> SEQUENCE: 4

```
Met Gly Asn Arg Arg Asp Leu Gly Gln Pro Arg Ala Gly Leu Cys Leu
  1               5                  10                  15

Leu Leu Ala Ala Leu Gln Leu Leu Pro Gly Thr Gln Ala Asp Pro Val
             20                  25                  30

Asp Val Leu Lys Ala Leu Gly Val Gln Gly Gly Gln Ala Gly Val Pro
         35                  40                  45

Glu Gly Pro Gly Phe Cys Pro Gln Arg Thr Pro Glu Gly Asp Arg Ala
     50                  55                  60

Phe Arg Ile Gly Gln Ala Ser Thr Leu Gly Ile Pro Thr Trp Glu Leu
 65                  70                  75                  80

Phe Pro Glu Gly His Phe Pro Glu Asn Phe Ser Leu Leu Ile Thr Leu
                 85                  90                  95

Arg Gly Gln Pro Ala Asn Gln Ser Val Leu Leu Ser Ile Tyr Asp Glu
            100                 105                 110

Arg Gly Ala Arg Gln Leu Gly Leu Ala Leu Gly Pro Ala Leu Gly Leu
        115                 120                 125

Leu Gly Asp Pro Phe Arg Pro Leu Pro Gln Gln Val Asn Leu Thr Asp
    130                 135                 140

Gly Arg Trp His Arg Val Ala Val Ser Ile Asp Gly Glu Met Val Thr
145                 150                 155                 160

Leu Val Ala Asp Cys Glu Ala Gln Pro Pro Val Leu Gly His Gly Pro
                165                 170                 175

Arg Phe Ile Ser Ile Ala Gly Leu Thr Val Leu Gly Thr Gln Asp Leu
            180                 185                 190

Gly Glu Lys Thr Phe Glu Gly Asp Ile Gln Glu Leu Leu Ile Ser Pro
        195                 200                 205

Asp Pro Gln Ala Ala Phe Gln Ala Cys Glu Arg Tyr Leu Pro Asp Cys
    210                 215                 220

Asp Asn Leu Ala Pro Ala Ala Thr Val Ala Pro Gln Gly Glu Pro Glu
225                 230                 235                 240

Thr Pro Arg Pro Arg Arg Lys Gly Lys Gly Lys Gly Arg Lys Lys Gly
                245                 250                 255

Arg Gly Arg Lys Gly Lys Gly Arg Lys Lys Asn Lys Glu Ile Trp Thr
            260                 265                 270

Ser Ser Pro Pro Pro Asp Ser Ala Glu Asn Gln Thr Ser Thr Asp Ile
        275                 280                 285

Pro Lys Thr Glu Thr Pro Ala Pro Asn Leu Pro Pro Thr Pro Thr Pro
    290                 295                 300

Leu Val Val Thr Ser Thr Val Thr Thr Gly Leu Asn Ala Thr Ile Leu
305                 310                 315                 320

Glu Gly Ser Leu Asp Pro Asp Ser Gly Thr Glu Leu Gly Thr Leu Glu
                325                 330                 335

Thr Lys Ala Ala Arg Glu Asp Glu Glu Gly Asp Asp Ser Thr Met Gly
            340                 345                 350

Pro Asp Phe Arg Ala Ala Glu Tyr Pro Ser Arg Thr Gln Phe Gln Ile
        355                 360                 365

Phe Pro Gly Ala Gly Glu Lys Gly Ala Lys Gly Glu Pro Ala Val Ile
    370                 375                 380

Glu Lys Gly Gln Gln Phe Glu Gly Pro Pro Gly Ala Pro Gly Pro Gln
385                 390                 395                 400
```

-continued

```
Gly Val Val Gly Pro Ser Gly Pro Pro Gly Pro Pro Gly Phe Pro Gly
            405                 410                 415

Asp Pro Gly Pro Pro Gly Pro Ala Gly Leu Pro Gly Ile Pro Gly Ile
        420                 425                 430

Asp Gly Ile Arg Gly Pro Pro Gly Thr Val Ile Met Met Pro Phe Gln
    435                 440                 445

Phe Ala Gly Gly Ser Phe Lys Gly Pro Pro Val Ser Phe Gln Gln Ala
    450                 455                 460

Gln Ala Gln Ala Val Leu Gln Gln Thr Gln Leu Ser Met Lys Gly Pro
465                 470                 475                 480

Pro Gly Pro Val Gly Leu Thr Gly Arg Pro Gly Pro Val Gly Leu Pro
            485                 490                 495

Gly His Pro Gly Leu Lys Gly Glu Glu Gly Ala Glu Gly Pro Gln Gly
        500                 505                 510

Pro Arg Gly Leu Gln Gly Pro His Gly Pro Pro Gly Arg Val Gly Lys
    515                 520                 525

Met Gly Arg Pro Gly Ala Asp Gly Ala Arg Gly Leu Pro Gly Asp Thr
    530                 535                 540

Gly Pro Lys Gly Asp Arg Gly Phe Asp Gly Leu Pro Gly Leu Pro Gly
545                 550                 555                 560

Glu Lys Gly Gln Arg Gly Asp Phe Gly His Val Gly Gln Pro Gly Pro
            565                 570                 575

Pro Gly Glu Asp Gly Glu Arg Gly Ala Glu Gly Pro Pro Gly Pro Thr
        580                 585                 590

Gly Gln Ala Gly Glu Pro Gly Pro Arg Gly Leu Leu Gly Pro Arg Gly
    595                 600                 605

Ser Pro Gly Pro Thr Gly Arg Pro Gly Val Thr Gly Ile Asp Gly Ala
    610                 615                 620

Pro Gly Ala Lys Gly Asn Val Gly Pro Pro Gly Glu Pro Gly Pro Pro
625                 630                 635                 640

Gly Gln Gln Gly Asn His Gly Ser Gln Gly Leu Pro Gly Pro Gln Gly
            645                 650                 655

Leu Ile Gly Thr Pro Gly Glu Lys Gly Pro Pro Gly Asn Pro Gly Ile
        660                 665                 670

Pro Gly Leu Pro Gly Ser Asp Gly Pro Leu Gly His Pro Gly His Glu
    675                 680                 685

Gly Pro Thr Gly Glu Lys Gly Ala Gln Gly Pro Pro Gly Ser Ala Gly
    690                 695                 700

Pro Pro Gly Tyr Pro Gly Pro Arg Gly Val Lys Gly Thr Ser Gly Asn
705                 710                 715                 720

Arg Gly Leu Gln Gly Glu Lys Gly Glu Lys Gly Glu Asp Gly Phe Pro
            725                 730                 735

Gly Phe Lys Gly Asp Val Gly Leu Lys Gly Asp Gln Gly Lys Pro Gly
        740                 745                 750

Ala Pro Gly Pro Arg Gly Glu Asp Gly Pro Glu Gly Pro Lys Gly Gln
    755                 760                 765

Ala Gly Gln Ala Gly Glu Glu Gly Pro Pro Gly Ser Ala Gly Glu Lys
    770                 775                 780

Gly Lys Leu Gly Val Pro Gly Leu Pro Gly Tyr Pro Gly Arg Pro Gly
785                 790                 795                 800

Pro Lys Gly Ser Ile Gly Phe Pro Gly Pro Leu Gly Pro Ile Gly Glu
            805                 810                 815
```

-continued

```
Lys Gly Lys Ser Gly Lys Thr Gly Gln Pro Gly Leu Glu Gly Glu Arg
            820                 825                 830

Gly Pro Pro Gly Ser Arg Gly Glu Arg Gly Gln Pro Gly Ala Thr Gly
        835                 840                 845

Gln Pro Gly Pro Lys Gly Asp Val Gly Gln Asp Gly Ala Pro Gly Ile
    850                 855                 860

Pro Gly Glu Lys Gly Leu Pro Gly Leu Gln Gly Pro Pro Gly Phe Pro
865                 870                 875                 880

Gly Pro Lys Gly Pro Pro Gly His Gln Gly Lys Asp Gly Arg Pro Gly
                885                 890                 895

His Pro Gly Gln Arg Gly Glu Leu Gly Phe Gln Gly Gln Thr Gly Pro
            900                 905                 910

Pro Gly Pro Ala Gly Val Leu Gly Pro Gln Gly Lys Thr Gly Glu Val
        915                 920                 925

Gly Pro Leu Gly Glu Arg Gly Pro Pro Gly Pro Pro Gly Pro Pro Gly
    930                 935                 940

Glu Gln Gly Leu Pro Gly Leu Glu Gly Arg Glu Gly Ala Lys Gly Glu
945                 950                 955                 960

Leu Gly Pro Pro Gly Pro Leu Gly Lys Glu Gly Pro Ala Gly Leu Arg
                965                 970                 975

Gly Phe Pro Gly Pro Lys Gly Gly Pro Gly Asp Pro Gly Pro Thr Gly
            980                 985                 990

Leu Lys Gly Asp Lys Gly Pro Pro Gly Pro Val Gly Ala Asn Gly Ser
        995                 1000                1005

Pro Gly Glu Arg Gly Pro Leu Gly Pro Ala Gly Gly Ile Gly Leu Pro
   1010                 1015                1020

Gly Gln Ser Gly Ser Glu Gly Pro Val Gly Pro Ala Gly Lys Lys Gly
1025                1030                1035                1040

Ser Arg Gly Glu Arg Gly Pro Pro Gly Pro Thr Gly Lys Asp Gly Ile
               1045                1050                1055

Pro Gly Pro Leu Gly Pro Leu Gly Pro Pro Gly Ala Ala Gly Pro Ser
           1060                1065                1070

Gly Glu Glu Gly Asp Lys Gly Asp Val Gly Ala Pro Gly His Lys Gly
       1075                1080                1085

Ser Lys Gly Asp Lys Gly Asp Ala Gly Pro Pro Gly Gln Pro Gly Ile
   1090                1095                1100

Arg Gly Pro Ala Gly His Pro Gly Pro Pro Gly Ala Asp Gly Ala Gln
1105                1110                1115                1120

Gly Arg Arg Gly Pro Pro Gly Leu Phe Gly Gln Lys Gly Asp Asp Gly
               1125                1130                1135

Val Arg Gly Phe Val Gly Val Ile Gly Pro Pro Gly Leu Gln Gly Leu
           1140                1145                1150

Pro Gly Pro Pro Gly Glu Lys Gly Glu Val Gly Asp Val Gly Ser Met
       1155                1160                1165

Gly Pro His Gly Ala Pro Gly Pro Arg Gly Pro Gln Gly Pro Thr Gly
   1170                1175                1180

Ser Glu Gly Thr Pro Gly Leu Pro Gly Gly Val Gly Gln Pro Gly Ala
1185                1190                1195                1200

Val Gly Glu Lys Gly Glu Arg Gly Asp Ala Gly Asp Pro Gly Pro Pro
               1205                1210                1215

Gly Ala Pro Gly Ile Pro Gly Pro Lys Gly Asp Ile Gly Glu Lys Gly
           1220                1225                1230

Asp Ser Gly Pro Ser Gly Ala Ala Gly Pro Pro Gly Lys Lys Gly Pro
```

-continued

```
        1235                1240                1245

Pro Gly Glu Asp Gly Ala Lys Gly Ser Val Gly Pro Thr Gly Leu Pro
    1250                1255                1260

Gly Asp Leu Gly Pro Pro Gly Asp Pro Gly Val Ser Gly Ile Asp Gly
1265                1270                1275                1280

Ser Pro Gly Glu Lys Gly Asp Pro Gly Asp Val Gly Gly Pro Gly Pro
                1285                1290                1295

Pro Gly Ala Ser Gly Glu Pro Gly Ala Pro Gly Pro Pro Gly Lys Arg
            1300                1305                1310

Gly Pro Ser Gly His Met Gly Arg Glu Gly Arg Glu Gly Glu Lys Gly
        1315                1320                1325

Ala Lys Gly Glu Pro Gly Pro Asp Gly Pro Pro Gly Arg Thr Gly Pro
    1330                1335                1340

Met Gly Ala Arg Gly Pro Pro Gly Arg Val Gly Pro Glu Gly Leu Arg
1345                1350                1355                1360

Gly Ile Pro Gly Pro Val Gly Glu Pro Gly Leu Leu Gly Ala Pro Gly
                1365                1370                1375

Gln Met Gly Pro Pro Gly Pro Leu Gly Pro Ser Gly Leu Pro Gly Leu
            1380                1385                1390

Lys Gly Asp Thr Gly Pro Lys Gly Glu Lys Gly His Ile Gly Leu Ile
        1395                1400                1405

Gly Leu Ile Gly Pro Pro Gly Glu Ala Gly Glu Lys Gly Asp Gln Gly
    1410                1415                1420

Leu Pro Gly Val Gln Gly Pro Pro Gly Pro Lys Gly Asp Pro Gly Pro
1425                1430                1435                1440

Pro Gly Pro Ile Gly Ser Leu Gly His Pro Gly Pro Pro Gly Val Ala
                1445                1450                1455

Gly Pro Leu Gly Gln Lys Gly Ser Lys Gly Ser Pro Gly Ser Met Gly
            1460                1465                1470

Pro Arg Gly Asp Thr Gly Pro Ala Gly Pro Pro Gly Pro Pro Gly Ala
        1475                1480                1485

Pro Ala Glu Leu His Gly Leu Arg Arg Arg Arg Arg Phe Val Pro Val
    1490                1495                1500

Pro Leu Pro Val Val Glu Gly Gly Leu Glu Glu Val Leu Ala Ser Leu
1505                1510                1515                1520

Thr Ser Leu Ser Leu Glu Leu Glu Gln Leu Arg Arg Pro Pro Gly Thr
                1525                1530                1535

Ala Glu Arg Pro Gly Leu Val Cys His Glu Leu His Arg Asn His Pro
            1540                1545                1550

His Leu Pro Asp Gly Glu Tyr Trp Ile Asp Pro Asn Gln Gly Cys Ala
        1555                1560                1565

Arg Asp Ser Phe Arg Val Phe Cys Asn Phe Thr Ala Gly Gly Glu Thr
    1570                1575                1580

Cys Leu Tyr Pro Asp Lys Lys Phe Glu Ile Val Lys Leu Ala Ser Trp
1585                1590                1595                1600

Ser Lys Glu Lys Pro Gly Gly Trp Tyr Ser Thr Phe Arg Arg Gly Lys
                1605                1610                1615

Lys Phe Ser Tyr Val Asp Ala Asp Gly Ser Pro Val Asn Val Val Gln
            1620                1625                1630

Leu Asn Phe Leu Lys Leu Leu Ser Ala Thr Ala Arg Gln Asn Phe Thr
        1635                1640                1645

Tyr Ser Cys Gln Asn Ala Ala Ala Trp Leu Asp Glu Ala Thr Gly Asp
    1650                1655                1660
```

-continued

```
Tyr Ser His Ser Ala Arg Phe Leu Gly Thr Asn Gly Glu Glu Leu Ser
1665                1670                1675                1680

Phe Asn Gln Thr Thr Ala Thr Thr Val Ser Val Pro Gln Asp Gly Cys
                1685                1690                1695

Arg Leu Arg Lys Gly Gln Thr Lys Thr Leu Phe Glu Phe Ser Ser Ser
            1700                1705                1710

Arg Ala Gly Phe Leu Pro Leu Trp Asp Val Ala Ala Thr Asp Phe Gly
        1715                1720                1725

Gln Thr Asn Gln Lys Phe Gly Phe Glu Leu Gly Pro Val Cys Phe Ser
    1730                1735                1740

Ser
1745


<210> SEQ ID NO 5
<211> LENGTH: 27
<212> TYPE: DNA
<213> ORGANISM: Bacteriophage lambda

<400> SEQUENCE: 5

tccccacctt ttgagcaagt tcagcct                                          27


<210> SEQ ID NO 6
<211> LENGTH: 28
<212> TYPE: DNA
<213> ORGANISM: Bacteriophage lambda

<400> SEQUENCE: 6

agattggggg taaataacag aggtggct                                         28


<210> SEQ ID NO 7
<211> LENGTH: 24
<212> TYPE: DNA
<213> ORGANISM: Homo sapiens

<400> SEQUENCE: 7

tgatcctaac caaggttgct cagg                                             24


<210> SEQ ID NO 8
<211> LENGTH: 24
<212> TYPE: DNA
<213> ORGANISM: Homo sapiens

<400> SEQUENCE: 8

gagtcagcgg aattcaggga cacg                                             24


<210> SEQ ID NO 9
<211> LENGTH: 23
<212> TYPE: DNA
<213> ORGANISM: Homo sapiens

<400> SEQUENCE: 9

aggcgaggtg atccagccac tgc                                              23


<210> SEQ ID NO 10
<211> LENGTH: 24
<212> TYPE: DNA
<213> ORGANISM: Homo sapiens

<400> SEQUENCE: 10

gctctctaac gggtaacagg ctcc                                             24
```

-continued

<210> SEQ ID NO 11
<211> LENGTH: 23
<212> TYPE: DNA
<213> ORGANISM: Homo sapiens

<400> SEQUENCE: 11
atgcaggaag atgaggccat acc 23

<210> SEQ ID NO 12
<211> LENGTH: 24
<212> TYPE: DNA
<213> ORGANISM: Homo sapiens

<400> SEQUENCE: 12
gctctctaac gggtaacagg ctcc 24

<210> SEQ ID NO 13
<211> LENGTH: 21
<212> TYPE: DNA
<213> ORGANISM: Mus musculus

<400> SEQUENCE: 13
ggagagctac gtggattatg c 21

<210> SEQ ID NO 14
<211> LENGTH: 21
<212> TYPE: DNA
<213> ORGANISM: Mus musculus

<400> SEQUENCE: 14
ccatcggaaa ggcacgtgtg g 21

<210> SEQ ID NO 15
<211> LENGTH: 22
<212> TYPE: DNA
<213> ORGANISM: Mus musculus

<400> SEQUENCE: 15
tgagcccacc ggtctccaga gc 22

<210> SEQ ID NO 16
<211> LENGTH: 21
<212> TYPE: DNA
<213> ORGANISM: Mus musculus

<400> SEQUENCE: 16
ccatcggaaa ggcacgtgtg g 21

<210> SEQ ID NO 17
<211> LENGTH: 23
<212> TYPE: DNA
<213> ORGANISM: Mus musculus

<400> SEQUENCE: 17
cttcaagaca cctgctctaa gcg 23

<210> SEQ ID NO 18
<211> LENGTH: 24
<212> TYPE: DNA
<213> ORGANISM: Mus musculus

<400> SEQUENCE: 18 acataccca tcatgtaagc tacc 24

-continued

```
<210> SEQ ID NO 19
<211> LENGTH: 24
<212> TYPE: DNA
<213> ORGANISM: Mus musculus

<400> SEQUENCE: 19

gtttggattt gaagtcggtc cagc                                              24


<210> SEQ ID NO 20
<211> LENGTH: 24
<212> TYPE: DNA
<213> ORGANISM: Mus musculus

<400> SEQUENCE: 20

tggcattact gaagcacgct gagg                                              24


<210> SEQ ID NO 21
<211> LENGTH: 22
<212> TYPE: DNA
<213> ORGANISM: Mus musculus

<400> SEQUENCE: 21

atgtggctta ccgtgtggca cg                                                22


<210> SEQ ID NO 22
<211> LENGTH: 24
<212> TYPE: DNA
<213> ORGANISM: Mus musculus

<400> SEQUENCE: 22

gctctgtggc ttatgaagtc ttgc                                              24


<210> SEQ ID NO 23
<211> LENGTH: 27
<212> TYPE: DNA
<213> ORGANISM: Mus musculus

<400> SEQUENCE: 23

cctggcaaga gggtgagtgg tcttcca                                           27


<210> SEQ ID NO 24
<211> LENGTH: 28
<212> TYPE: DNA
<213> ORGANISM: Mus musculus

<400> SEQUENCE: 24

gcatccaggt ttatgtcaag agtgggct                                          28
```